US011993503B2

(12) United States Patent
Hayakawa et al.

(10) Patent No.: US 11,993,503 B2
(45) Date of Patent: May 28, 2024

(54) ASEPTIC FILLER AND METHOD FOR CLEANING THE SAME

(71) Applicant: Dai Nippon Printing Co., Ltd., Tokyo (JP)

(72) Inventors: Atsushi Hayakawa, Tokyo (JP); Shuta Ito, Tokyo (JP)

(73) Assignee: Dai Nippon Printing Co., Ltd., Tokyo (JP)

(*) Notice: Subject to any disclaimer, the term of this patent is extended or adjusted under 35 U.S.C. 154(b) by 700 days.

(21) Appl. No.: 17/258,275

(22) PCT Filed: Aug. 28, 2019

(86) PCT No.: PCT/JP2019/033768
§ 371 (c)(1),
(2) Date: Jan. 6, 2021

(87) PCT Pub. No.: WO2020/045521
PCT Pub. Date: Mar. 5, 2020

(65) Prior Publication Data
US 2021/0269298 A1 Sep. 2, 2021

(30) Foreign Application Priority Data
Aug. 31, 2018 (JP) .................................. 2018-163610

(51) Int. Cl.
*B67C 7/00* (2006.01)
*A61L 2/20* (2006.01)
(Continued)

(52) U.S. Cl.
CPC .............. *B67C 7/0073* (2013.01); *A61L 2/20* (2013.01); *A61L 2/202* (2013.01); *A61L 2/208* (2013.01);
(Continued)

(58) Field of Classification Search
CPC .............................. B67C 7/0073; B67C 3/001
See application file for complete search history.

(56) References Cited

U.S. PATENT DOCUMENTS 8,181,429 B2 * 5/2012 Iwashita ................. B67C 3/045
53/425
8,621,824 B2 * 1/2014 Mielnik ................... B65B 55/18
53/425
(Continued)

FOREIGN PATENT DOCUMENTS

EP 2 921 450 A1 9/2015
EP 2 937 309 A1 10/2015
(Continued)

OTHER PUBLICATIONS

International Search Report and Written Opinion (Application No. PCT/JP2019/033768) dated Nov. 19, 2019.

*Primary Examiner* — Gloria R Weeks
(74) *Attorney, Agent, or Firm* — BURR PATENT LAW, PLLC

(57) ABSTRACT

Provided is an aseptic filler that includes no other sterilization apparatus for producing aseptic water than a sterilization apparatus for sterilizing a content, and a method for cleaning the same.
An aseptic water supply apparatus that supplies aseptic water, which is sterilized by a content sterilization apparatus that sterilizes a content, to at least a filling portion chamber is provided, and rinsing aseptic water for washing away a sterilizer when performing an SOP treatment of each chamber is supplied to each chamber.

20 Claims, 10 Drawing Sheets

(51) Int. Cl.
*A61L 2/22* (2006.01)
*B67C 3/00* (2006.01)
*B67C 3/22* (2006.01)

(52) U.S. Cl.
CPC ............... *A61L 2/22* (2013.01); *B67C 3/001* (2013.01); *B67C 3/22* (2013.01); *B67C 7/004* (2013.01); *A61L 2202/17* (2013.01)

(56) References Cited

U.S. PATENT DOCUMENTS

| | | | | |
|---|---|---|---|---|
| 9,751,742 | B2* | 9/2017 | Hayakawa | B67C 7/0073 |
| 10,384,240 | B2* | 8/2019 | Hayakawa | B08B 3/10 |
| 10,442,669 | B2* | 10/2019 | Hayakawa | B08B 9/027 |
| 11,014,797 | B2* | 5/2021 | Hayakawa | A61L 2/18 |
| 11,667,505 | B2* | 6/2023 | Hayakawa | A61L 2/26 53/426 |
| 11,708,257 | B2* | 7/2023 | Hayakawa | B67C 3/001 134/22.11 |
| 2002/0083682 | A1* | 7/2002 | Edwards | B65B 55/025 53/167 |
| 2003/0165400 | A1* | 9/2003 | Hayakawa | A61L 2/04 422/292 |
| 2007/0193222 | A1* | 8/2007 | Till | B67C 7/0073 53/167 |
| 2009/0007522 | A1* | 1/2009 | Sakai | A23F 3/163 53/426 |
| 2009/0320415 | A1* | 12/2009 | Senbon | B67C 7/0073 53/469 |
| 2010/0037984 | A1* | 2/2010 | Hiroya | B67C 7/0073 141/37 |
| 2010/0170867 | A1 | 7/2010 | Hayakawa | |
| 2011/0094616 | A1* | 4/2011 | Hayakawa | B65B 55/10 141/85 |
| 2011/0289883 | A1* | 12/2011 | Neubauer | B67C 7/0013 53/235 |
| 2012/0000492 | A1* | 1/2012 | Katzenbacher | B08B 9/02 134/99.1 |
| 2012/0102883 | A1* | 5/2012 | Raniwala | B67C 7/0073 53/425 |
| 2014/0109521 | A1* | 4/2014 | Hayakawa | B67C 3/242 53/558 |
| 2014/0109529 | A1* | 4/2014 | Hayakawa | B65B 3/022 53/558 |
| 2015/0298178 | A1* | 10/2015 | Hayakawa | B67C 7/0073 134/22.1 |
| 2016/0046475 | A1* | 2/2016 | Hayakawa | B67C 3/005 134/22.18 |
| 2016/0257055 | A1* | 9/2016 | Hayakawa | A61L 2/208 |
| 2018/0208446 | A1 | 7/2018 | Hayakawa et al. | |

FOREIGN PATENT DOCUMENTS

| | | |
|---|---|---|
| JP | 2000-153245 A1 | 6/2000 |
| JP | 2007-022600 A1 | 2/2007 |
| JP | 2007-331801 A1 | 12/2007 |
| JP | 2010-189034 A1 | 9/2010 |
| JP | 2011-255938 A1 | 12/2011 |
| JP | 2013-209164 A1 | 10/2013 |
| JP | 6056930 B1 | 1/2017 |
| JP | 2017-154822 A1 | 9/2017 |

* cited by examiner

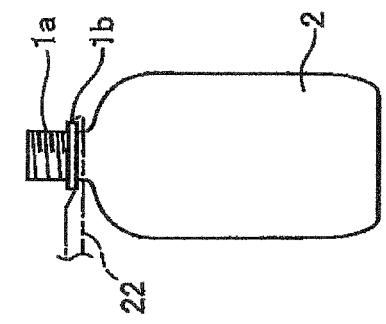
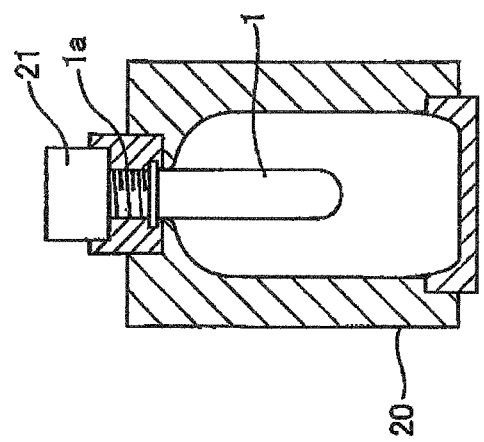
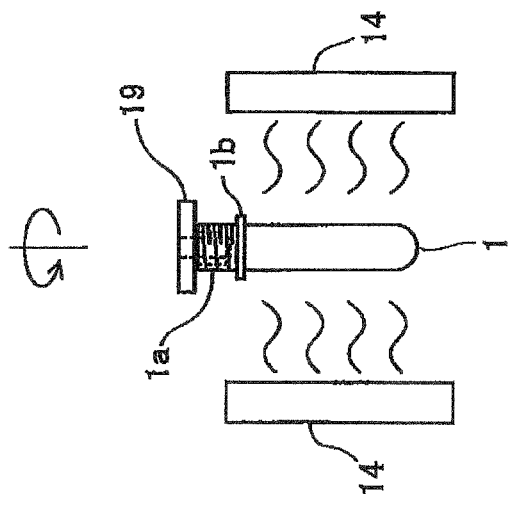
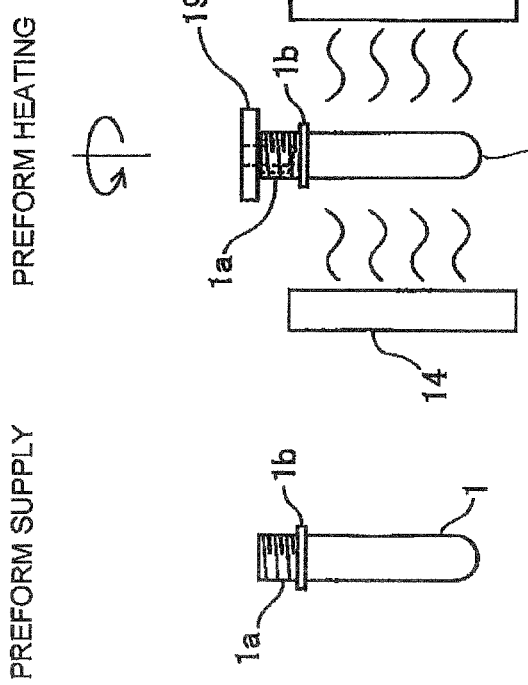

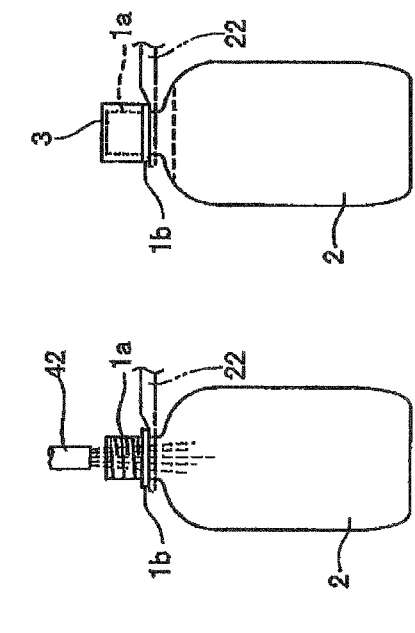
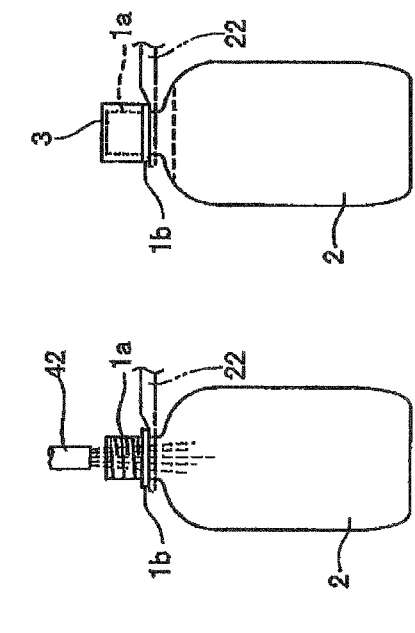
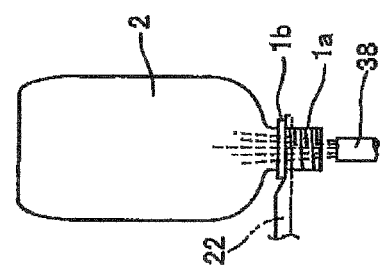
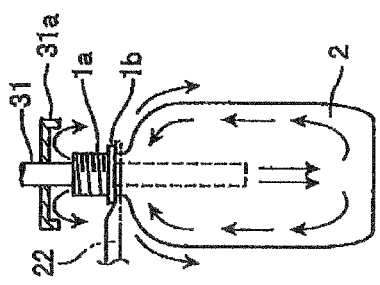
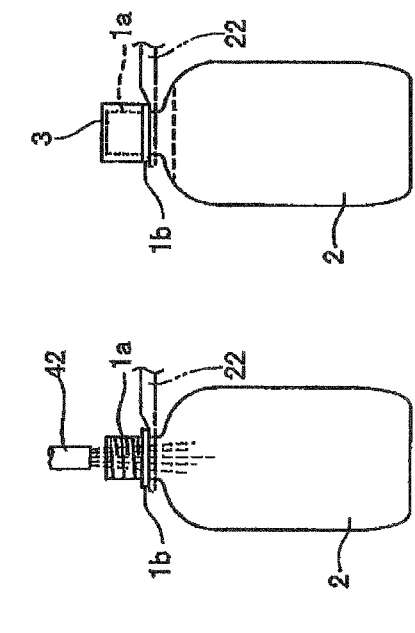
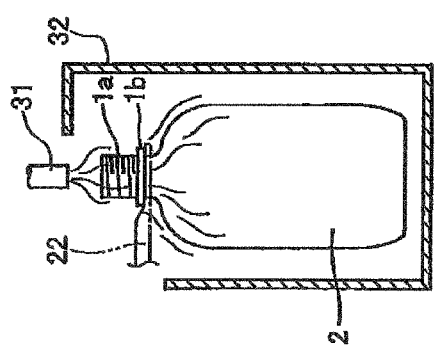

AIR BLASTING

STERILIZER GAS BLASTING ized and brought into an aseptic state (Patent Literature
ASEPTIC FILLER AND METHOD FOR CLEANING THE SAME

TECHNICAL FIELD

The present invention relates to an aseptic filler for filling a container such as a PET bottle with a drink, and a method for cleaning the same.

BACKGROUND ART

Conventionally, when the kind of drink to be filled in a container such as a bottle is switched, for example, from a current drink which is a tea drink, to milk coffee in an aseptic filler of drinks, the interior of the drink supply piping of the aseptic filler is first subjected to a CIP (Cleaning in Place) treatment, and next to an SIP (Sterilizing in Place) treatment (see Patent Literature 1).

The CIP treatment is performed by flowing a cleaning solution of water to which an alkaline chemical agent such as caustic soda is added, through a flow path from the interior of a pipe line of a drink filling path to a filling nozzle of the filler, and thereafter flowing a cleaning solution of water to which an acidic chemical agent is added. As a result of this, any remainder of the previously used drink or the like adhering to the inside of the drink filling path is removed (see Patent Literatures 1, 2, and 3).

The SIP treatment is performed by, for example, flowing steam and hot water or the like through the flow path which has been cleaned by the above-described CIP treatment. As a result of this, the interior of the drink filling path is sterilized and brought into an aseptic state (Patent Literature 1).

Further, there is arranged in the aseptic filler, a filler for automatically filling a container with a drink, and this filler is surrounded by an aseptic chamber which is capable of maintaining the interior of the chamber in an aseptic atmosphere, thereby being isolated from the outside. Since splashes of the drink which was filled in the previous filling operation, or the like adhere to the inside of the aseptic chamber, when the kind of drink to be filled is switched, the interior of the aseptic chamber is subjected to a COP (Cleaning out of Place) treatment to remove splashes of drink adhering to the inner wall of the aseptic chamber, the outer surface of equipment such as a filler in the aseptic chamber, or the like in the previous filling operation, from the interior of the aseptic chamber. The COP treatment is performed by, for example, spraying water, etc. like a shower into the aseptic chamber (see Patent Literature 4).

Further, since there is also a risk that bacteria enter into the aseptic chamber during various operation when switching the kind of drink, an SOP (Sterilizing out of Place) treatment is also performed on the interior of the aseptic chamber. The SOP treatment is performed by, for example, supplying a hydrogen peroxide solution in a mist or shower form into the aseptic chamber, and thereafter blasting hot air into the aseptic chamber to dry remaining hydrogen peroxide that has remained (see Patent Literature 4).

When performing the COP treatment and the SOP treatment, aseptic water is sprayed into the aseptic chamber for washing the cleaning agent and sterilizer away. The aseptic filler is provided with a sterilization apparatus for sterilizing the drink to be filled. Further, a sterilization apparatus for sterilizing water by heating is also provided to produce aseptic water to be used when performing the COP treatment and the SOP treatment (see Patent Literature 5).

In a conventional aseptic filler, cleaning of the interior of the container after sterilization, cleaning of the cap after sterilization, and cleaning of the outer surface of the container mouth portion after drink filling are necessary, and a large amount of aseptic water is used for these processes so that a sterilization apparatus for producing aseptic water is necessary in addition to the sterilization apparatus for sterilizing the drink. However, due to use of a gas or mist of gasified sterilizer, or a mixture thereof for sterilization of the container and the cap, the cleaning of the interior of the container after sterilization and the cleaning of the cap after sterilization have become unnecessary, and also the cleaning of the outer surface of the container mouth portion after drink filling has become unnecessary due to improvement of the filling nozzle.

CITATION LIST

Patent Literature

Patent Literature 1: Japanese Patent Laid-Open No. 2007-22600
Patent Literature 2: Japanese Patent Laid-Open No. 2007-331801
Patent Literature 3: Japanese Patent Laid-Open No. 2000-153245
Patent Literature 4: Japanese Patent No. 6056930
Patent Literature 5: Japanese Patent Laid-Open No. 2010-189034

SUMMARY OF INVENTION

Technical Problem

In a conventional aseptic filler, cleaning of the interior of the container after sterilization, cleaning of the cap after sterilization, and cleaning of the outer surface of the mouth portion of the container after drink filling are necessary so that a large amount of aseptic water is used for these processes. Further, when the SOP treatment is performed, aseptic water is sprayed into the chamber to wash away the cleaning agent and the sterilizer. In order to produce aseptic water to be used when performing the SOP treatment to be performed before operation of the aseptic filler, and aseptic water to be used for cleaning of the interior of the container after sterilization at the time of operation of the aseptic filler, cleaning of the cap after sterilization, and cleaning of the outer surface of the container mouth portion after drink filling, a sterilization apparatus for producing aseptic water is required in addition to the sterilization apparatus for sterilizing the drink. A sterilization apparatus that sterilizes water by heating to produce aseptic water is expensive, and therefore is a burden of initial investment.

Due to improvements of the sterilization method and filling method in the aseptic filler, cleaning of the interior of the container after sterilization, cleaning of the cap after sterilization, and cleaning of the outer surface of the container mouth portion after drink filling have become unnecessary so that the aseptic water to be used while operation of the aseptic filler has become not always necessary.

However, when performing the SOP treatment before the operation of the aseptic filler, aseptic water for washing the cleaning agent and the sterilizer away is necessary, and the aseptic filler needs to be equipped with a sterilization apparatus for producing aseptic water for performing the SOP treatment. Equipping the aseptic filler with a sterilization apparatus for producing aseptic water for performing the SOP treatment in addition to the sterilization apparatus for sterilizing the drink has made the initial investment of the aseptic filler excessive, and there is a need for an aseptic filler that does not need to be equipped with such a sterilization apparatus.

An object of the present invention is to provide an aseptic filler which is not provided with a sterilization apparatus for producing aseptic water to be used for the SOP treatment in addition to the sterilization apparatus for sterilizing the drink, and a method for cleaning the same.

Solution to Problem

The aseptic filler according to the present invention is an aseptic filler, sequentially including: a filling portion that fills a container sterilized with an aseptic atmosphere, with a content sterilized by a content sterilization apparatus; and a sealing portion that seals the container filled with the content, with a sterilized lid material in an aseptic atmosphere; and further includes a filling portion chamber that shields at least the filling portion, wherein the aseptic filler includes an aseptic water supply apparatus that supplies aseptic water which is sterilized by the content sterilization apparatus at least to the filling portion chamber of the aseptic filler.

Moreover, in the aseptic filler according to the present invention, preferably, the aseptic water supply apparatus includes a heating apparatus that heats the aseptic water.

Further, in the aseptic filler according to the present invention, preferably, the aseptic water supply apparatus includes a sterilization apparatus that sterilizes an interior of aseptic water supply piping for supplying the aseptic water from the content sterilization apparatus to at least the filling portion chamber.

Furthermore, in the aseptic filler according to the present invention, preferably, two or more of the content sterilization apparatuses are provided.

Furthermore, in the aseptic filler according to the present invention, preferably, the aseptic water supply apparatus is provided with an aseptic water reservoir tank that stores the aseptic water.

A method for cleaning aseptic filler according to the present invention is a method for cleaning an aseptic filler, the aseptic filler sequentially including: a filling portion that fills a container sterilized with an aseptic atmosphere, with a content sterilized by a content sterilization apparatus; and a sealing portion that seals the container filled with the content, with a sterilized lid material in an aseptic atmosphere; and further includes a filling portion chamber that shields at least the filling portion, wherein at least an interior of the filling portion chamber is cleaned by supplying aseptic water sterilized by the content sterilization apparatus.

Further, in the method for cleaning an aseptic filler according to the present invention, preferably, the aseptic water supplied from the aseptic water supply apparatus is heated.

Furthermore, in the method for cleaning the aseptic filler according to the present invention, preferably, the interior of aseptic water supply piping for supplying the aseptic water from the content sterilization apparatus to at least the filling portion chamber is sterilized with a sterilizer.

Furthermore, in the method for cleaning the aseptic filler according to the present invention, preferably, the aseptic water is supplied from at least one of two or more of the content sterilization apparatuses.

Furthermore, in the method for cleaning the aseptic filler according to the present invention, preferably, the aseptic water is stored and thereafter supplied.

Advantageous Effects of Invention

According to the present invention, there is no need of providing a sterilization apparatus for producing aseptic water used for the SOP treatment of the aseptic filler, and thus the initial investment of the aseptic filler can be suppressed. Further, since the interior of the chamber that should be brought into an aseptic atmosphere before operation of the aseptic filler can be cleaned with the aseptic water produced by the content sterilization apparatus that sterilizes the content, the content sterilization apparatus will be operated even before the aseptic filler is operated, and the number of cases where the content sterilization apparatus is stopped and cooled when the aseptic filler is stopped is reduced so that energy efficiency is improved and running cost can be suppressed compared to a case in which a separate sterilizer is provided for the production of aseptic water.

BRIEF DESCRIPTION OF THE DRAWINGS

FIG. 2 is a diagram showing the process steps of a heating portion and a molding portion of the aseptic filler according to Embodiment 1 of the present invention, in which (A) shows a preform supply step, (B) a preform heating step, (C) a blow molding step, and (D) a container taking-out step.

FIG. 3 is a diagram showing the process steps of a sterilizing portion and a filling portion of the aseptic filler according to Embodiment 1 of the present invention, in which (E-1) shows a sterilizer gas blasting step which is performed with the container being shielded by a tunnel, (E-2) a sterilizer gas blasting step which is performed with the sterilizer gas blasting nozzle being inserted into the container, (F-1) an air rinsing step with the container being kept in an upright state, (F-2) an air rinsing step with the container being kept in an inverted state, (G) a filling step, and (H) a sealing step.

DESCRIPTION OF EMBODIMENTS

In the following, embodiments for practicing the present invention will be described with reference to the drawings.

Embodiment 1

Figure 1:
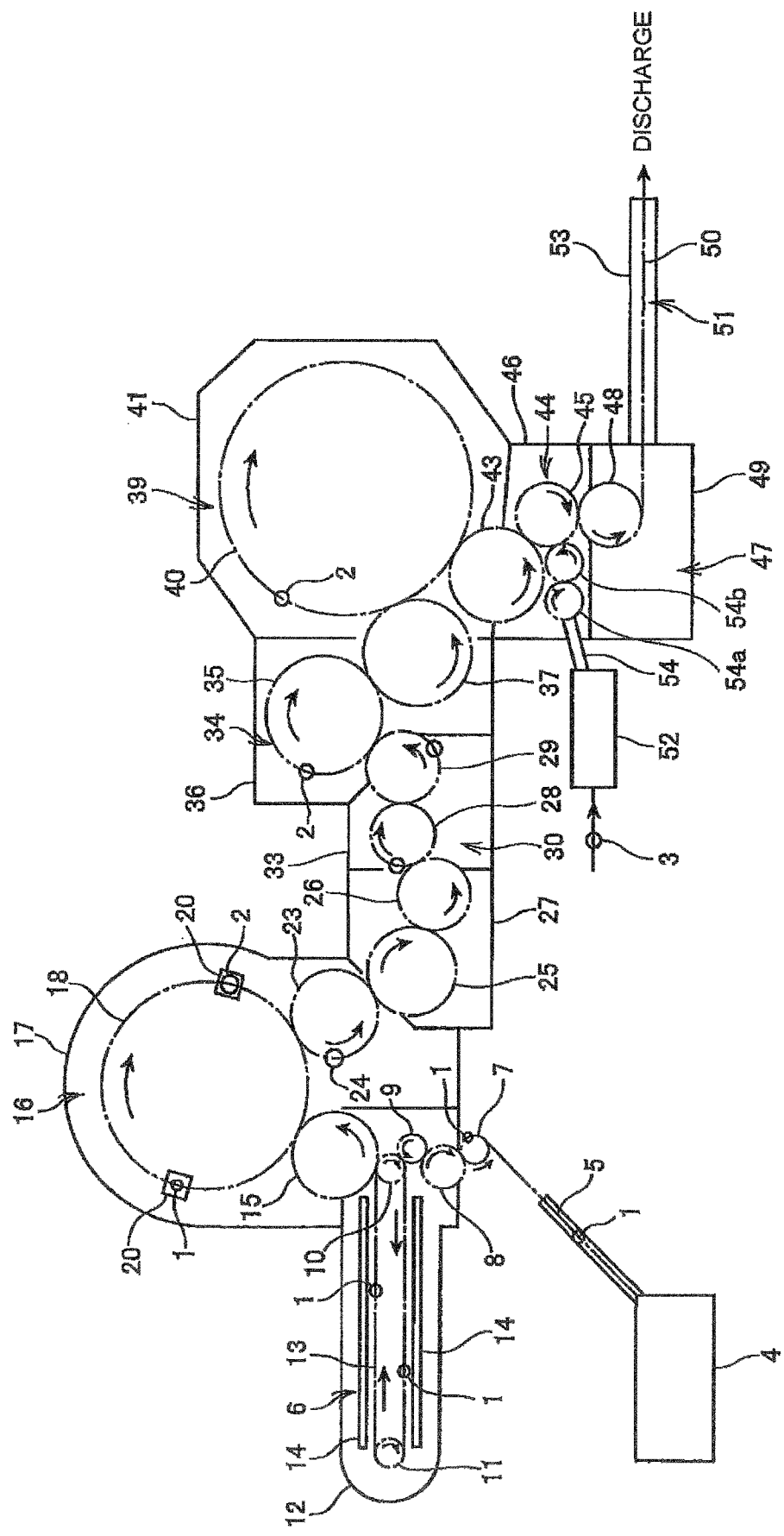
FIG. 1 is a plan view showing an outline of an aseptic filler according to Embodiment 1 of the present invention.

An aseptic filler according to Embodiment 1 of the present invention will be shown in FIG. 1. An outline of the aseptic filler, which is an aseptic filler for sterilizing containers, and includes: a heating portion of a preform supplied; a molding portion from the preform into a container; an inspecting portion of the molded container; a container sterilizing portion that sterilizes the container; an air rinsing portion of the sterilized container; a filling portion that fills the sterilized container with a content sterilized by the content sterilization apparatus in an aseptic atmosphere; a sealing portion that seals the container filled with the content with a sterilized lid material in an aseptic atmosphere; and a discharging portion that discharges the sealed container is described by using FIG. 1. Details of each portion will be described by using FIGS. 2, 3, 4, and 5, and an aseptic water supply apparatus to be used when performing an SOP treatment in a chamber that shields each portion will be described by using FIGS. 6, 7, and 8. According to Embodiment 1, aseptic water to be used for the COP treatment or the SOP treatment in the chamber, which should be kept in an aseptic atmosphere, of the aseptic filler can be supplied by a content sterilization apparatus that sterilizes the content so that initial investment can be suppressed, and energy consumption during running can be reduced.

Outline of Embodiment 1

As shown in FIG. 1, an aseptic filler according to Embodiment 1 includes: a preform supply apparatus 4 that supplies a preform 1; a heating portion 6 that heats the preform 1 to a temperature for molding the same into a container 2; a molding portion 16 that molds the heated preform 1 into the container 2; an inspection wheel 23 that inspects the molded container; a container sterilizing portion 30 that sterilizes the molded container 2; an air rinsing portion 34 that air rinses the sterilized container 2; a filling portion 39 that fills the air-rinsed container 2 with the sterilized content in an aseptic atmosphere; a lid-material sterilizing portion 52 that sterilizes a lid material 3 which is a sealing member; a sealing portion 44 that seals the container 2 filled with the content, with the sterilized lid material 3 in an aseptic atmosphere; a discharging portion 47 that places the sealed container 2 on a discharging conveyor 50; and an outlet portion 51 that causes the container 2 to be discharged to a non-aseptic zone with the discharging conveyor 50. Here, the inspection wheel 23 and the air rinsing portion 34 may not be included.

The heating portion 6 is shielded by the heating portion chamber 12; the molding portion 16 and the inspection wheel 23 by a molding portion chamber 17; the container sterilizing portion 30 by a container sterilizing portion chamber 33; the air rinsing portion 34 by an air rinsing portion chamber 36; the filling portion 39 by a filling portion chamber 41; the sealing portion 44 by a sealing portion chamber 46; the discharging portion 47 by a discharging portion chamber 49; and the outlet portion 51 by an outlet portion chamber 53, respectively. An atmosphere shut-off chamber 27 is provided between the molding portion chamber 17 and the container sterilizing portion chamber 33 such that a gas or mist, or a mixture thereof, of the sterilizer generated in the container sterilizing portion 30 does not flow into the molding portion 16. The gas or mist, or a mixture thereof, of the sterilizer generated in the container sterilizing portion chamber 33 will not flow into the molding portion chamber 17 as a result of the atmosphere shut-off chamber 27 being exhausted. Here, the heating portion 6 and the molding portion 16 may be shielded by a single chamber. Moreover, the lid-material sterilizing portion 52 and the sealing portion 44 may also be shielded by a single chamber. Further, the sealing portion 44 and the discharging portion 47 may also be shielded by a single chamber.

During operation of the aseptic filler, aseptic air filtered by a aseptic filter is supplied to the container sterilizing portion chamber 33, the air rinsing portion chamber 36, the filling portion chamber 41, the sealing portion chamber 46, the discharging portion chamber 49 and the outlet portion chamber 53 so that the aseptic condition of the aseptic filler is maintained by making the pressure in each chamber positive. The pressure for keeping apositive pressure is set highest in the filling portion chamber 41, and is set lower toward the air rinsing portion chamber 36 and the container sterilizing portion chamber 33 in the upstream direction. Further, the pressure is set lower toward the sealing portion chamber 46, the discharging portion chamber 49, and the outlet portion chamber 53 in the downstream direction. As a result of the atmosphere shut-off chamber 27 being exhausted, the pressure in the atmosphere is shut-off chamber 27 is kept substantially the same as the atmospheric pressure. For example, if the pressure in the filling portion chamber 41 is 20 to 40 Pa, the pressure in the other chambers will be lower than the pressure in the filling portion chamber 41.

The interiors of the container sterilizing portion chamber 33, the air rinsing portion chamber 36, the filling portion chamber 41, the sealing portion chamber 46, the discharging portion chamber 49 and the outlet portion chamber 53, which should keep an aseptic atmosphere during operation of the aseptic filler, are sterilized before operation of the aseptic filler. That is, the SOP treatment is performed. Thereafter, aseptic air is supplied, and thereby the interior of each chamber is kept in an aseptic atmosphere. Since a gas or mist, or a mixture thereof, of the sterilizer is blasted during operation of the aseptic filler, the container sterilizing portion chamber 33 may not be sterilized before operation of the aseptic filler.

Although the preform 1 is supplied to the aseptic filler, and is molded into the container 2 in the aseptic filler in Embodiment 1, the molded container 2 may be supplied to the container sterilizing portion 30 in the aseptic filler.

Details of Embodiment 1

First, a preform 1 shown in FIG. 2(A) is conveyed continuously at a desired speed from a preform supply apparatus 4 shown in FIG. 1 to a heating portion 6 by a preform supply conveyor 5.

The preform 1 in the present embodiment is a bottomed tubular body having a test tube shape, and is given a mouth portion 1a similar to that of the container 2 shown in FIG. 2(D) in the beginning of its molding. A male screw is formed in the mouth portion 1a at the same time as the molding of the preform 1. Further, the preform 1 is formed with a support ring 1b for conveyance in the lower portion of the mouth portion 1a. The preform 1 or the container 2 is gripped by a gripper 22 via the support ring 1*b*, and travels in the aseptic filler. The preform 1 is molded by injection molding, compression molding, or the like. The material of the preform 1 is made of a thermoplastic resin such as polyethylene terephthalate, polyethylene naphthalate, polypropylene, and polyethylene, and these resins may be used alone or as a mixture, and may contain a recycled thermoplastic resin. Further, in order to impart barrier properties, a thermoplastic resin, such as an ethylene-vinyl alcohol copolymer and a polyamide having an aromatic amine as a monomer such as m-xylylenediamine, may be contained as a layer or as a mixture.

The preform 1 supplied to the heating portion 6 is conveyed by a wheel 7, 8 which is provided with a large number of grippers 22 at a constant pitch, to reach a heating portion conveying wheel 9. Here, the preform 1 is released from the gripper 22 as shown in FIG. 2(B), and is conveyed with the spindle 19 being inserted into the mouth portion 1*a* of the preform 1.

As shown in FIG. 2(B), the preform 1 is heated to a temperature suitable for later blow molding by an infrared heater 14 or another heating device. This temperature is preferably 90° C. to 130° C.

Note that the temperature of the mouth portion 1*a* of the preform 1 is suppressed to be 70° C. or less to prevent deformation or the like.

As shown in FIG. 2(B), with a spindle 19 being inserted into the mouth portion 1*a*, the preform 1 is heated by the infrared heater 14 and is conveyed while being rotated by an endless chain 13. The spindle 19 is provided on the endless chain 13 at a regular interval. The endless chain 13 is rotated by pulleys 10 and 11. By inserting a mandrel, instead of the spindle 19, into the preform 1, the preform 1 can be conveyed while being rotated in an inverted state.

The heated preform 1 is released from the spindle 19, is gripped by the gripper 22, and is conveyed to a molding wheel 18 of a molding portion 16 via a wheel 15. As shown in FIG. 2(C), the preform 1 is blow molded into the container 2 by a die 20 provided on the molding wheel 18. A plurality of dies 20 and blow nozzles 21 are arranged around the molding wheel 18, and rotate around the molding wheel 18 at a constant speed as the molding wheel 18 rotates. When the heated preform 1 arrives, the die 20 sandwiches the preform 1. Subsequently, the blow nozzle 21 is joined to the preform 1, and an extension rod (not shown) is guided into a hole provided in the blow nozzle 21, and is inserted into the preform 1. The extension rod to be inserted elongates the bottom of the preform 1, so that the preform 1 is length wisely elongated, and at the same time, a gas such as air is blown into the preform 1 from a blow nozzle 21, and the preform 1 is crosswisely elongated. The preform 1 is lengthwisely and crosswisely elongated in the die 20 to form the container 2. As shown in FIG. 2(D), the molded container 2 is taken out from the die 20, and is passed to the inspection wheel 23 with the support ring 1*b* being gripped by the gripper 22 provided on the inspection wheel 23.

The molded container 2 is inspected for the container temperature, the container body portion, the support ring 1*b*, the top surface of container mouth portion, the container bottom portion, etc. by inspection equipment 24 provided around the inspection wheel 23 and, when determined to be abnormal, the molded container 2 is discharged to the outside of the aseptic filler by a discharge apparatus (not shown). While the inspection of the container is performed in the molding portion chamber 17, the inspecting portion may be shielded by a separate chamber.

In the container temperature inspection, the surface temperature of the container 2 is inspected to determine the quality of the container 2. The temperature sensor is, for example, an infrared radiation thermometer (infrared radiation camera), but other thermometers can also be used. It is necessary that the residual heat at the time of container molding remains in the container 2 for the purpose of sterilizing the container 2 properly. The temperature detected by the temperature sensor is preferably 50° C. or more.

Further, images of the container body portion, the support ring 1*b*, the top surface of the container mouth portion, and the container bottom portion are picked up by a camera, and the state of each part is inspected. The taken image is processed by an image processing apparatus, and the presence or absence of abnormalities such as scratches, foreign matters, deformation, and discoloration is determined. A container 2 that exceeds a permissible range is determined to be abnormal.

The container 2 which has not been determined to be abnormal by the inspection with the inspection equipment 24 is conveyed to a container sterilizing portion 30 via the wheel 25, 26 in the atmosphere shut-off chamber 27 provided between the molding portion 16 and the container sterilizing portion 30 such that a gas or mist, or a mixture thereof, of the sterilizer generated in the container sterilizing portion 30 does not flow into the molding portion 16.

The container 2 conveyed to the container sterilizing portion 30 is sterilized in the wheel 28. FIG. 3(E-1) shows a gas blasting step of a sterilizer onto the container 2 for sterilizing the container 2. A sterilizer gas blasting nozzle 31 is provided for blasting the gas of the sterilizer onto the container 2. The sterilizer gas blasting nozzle 31 is fixed such that the nozzle hole at the tip thereof can face the opening of the mouth portion 1*a* of the container 2 that travels directly below. Further, if necessary, a sterilizer gas blasting tunnel 32 is provided below the sterilizer gas blasting nozzle 31 along the traveling path of the container 2 as shown in FIG. 3(E-1). The number of the sterilizer gas blasting nozzles 31 may be one or plural. The gas of the sterilizer blasted onto the container 2 flows into the inside of the container 2 and sterilizes the inner surface of the container 2. At this time, the container 2 travels in the sterilizer gas blasting tunnel 32, and thereby a gas or mist, or a mixture thereof, of the sterilizer also flows to the outer surface of the container 2 so that the outer surface of the container 2 is sterilized.

Further, as shown in FIG. 3(E-2), the sterilizer gas blasting nozzle 31 is made to follow the conveyance of the container 2, and the sterilizer gas blasting nozzle 31 is inserted into the container 2, and a gas or mist, or a mixture thereof, of the sterilizer may be blasted directly onto the inner surface the container 2. The gas or mist, or a mixture thereof, of the sterilizer overflowing from the container 2 collides with a guide member 31*a* provided surrounding the sterilizer gas blasting nozzle 31, and flows to the outer surface of the container 2, thus coming into contact with the outer surface of the container 2. The guide member 31*a* is provided with a flange portion coaxial with the sterilizer gas blasting nozzle 31 and an annular wall portion protruding from the flange portion to the outer periphery.

Figure 4:
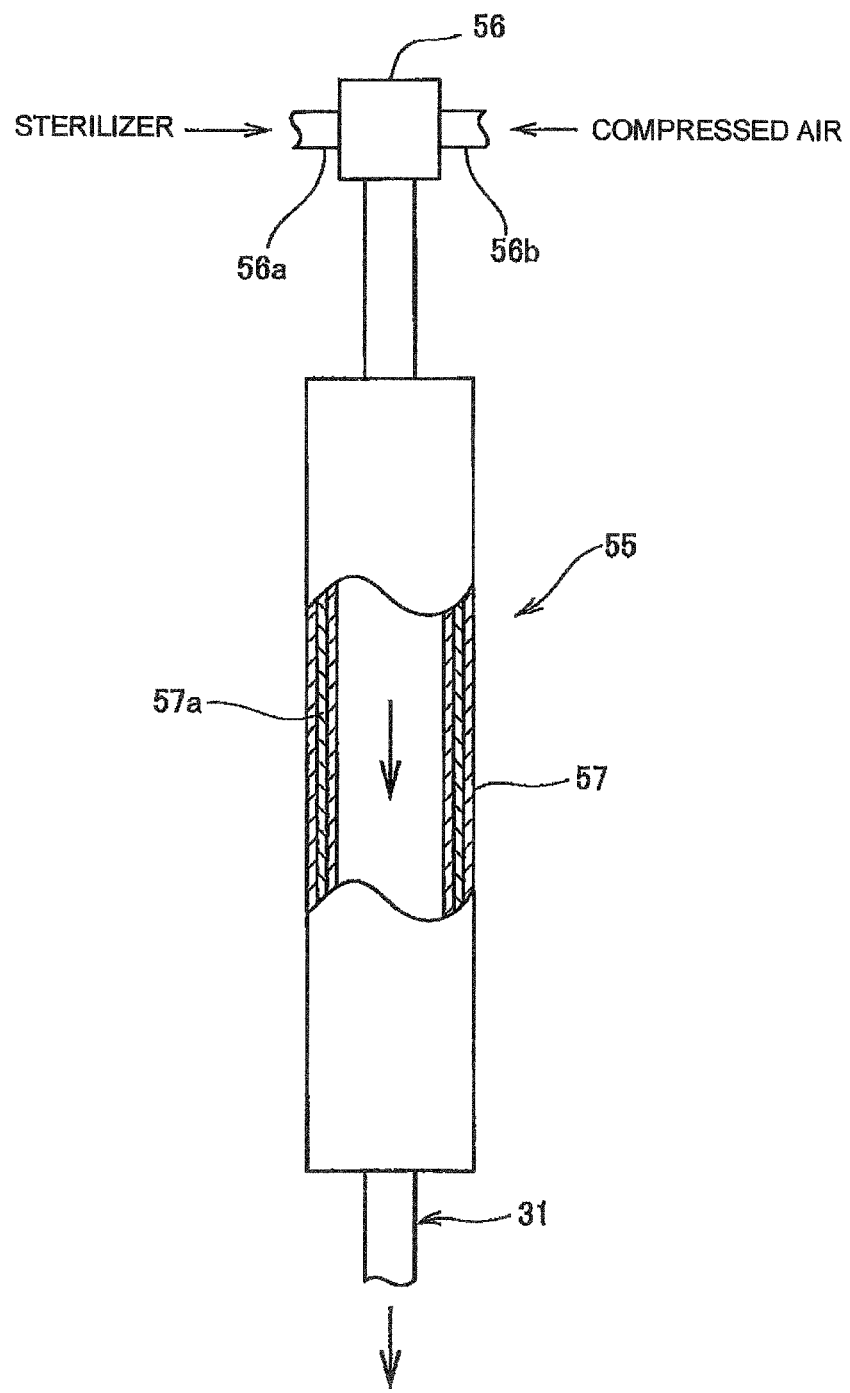
FIG. 4 is a diagram showing a sterilizer gas generator which is incorporated in the aseptic filler according to Embodiment 1 of the present invention.

The gas or mist, or a mixture thereof, of the sterilizer is a mist or a mixture thereof, which is formed by the sterilizer to be gasified, or the gasified sterilizer being condensed by the sterilizer gas generator 55 shown in FIG. 4. The sterilizer gas generator 55 includes a sterilizer supplying portion 56 which is a twin-fluid spray nozzle that supplies the sterilizer in the form of droplets, and a vaporizing portion 57 that heats the sterilizer supplied from the sterilizer supplying portion 56 to a decomposition temperature or less to vaporize the same. The sterilizer supplying portion 56 introduces the sterilizer and compressed air from the sterilizer supply path 56a and the compressed air supply path 56b, respectively, and sprays the sterilizer into the vaporizing portion 57. The vaporizing portion 57 is a pipe in which a heater 57a is interposed between the inner and outer walls, and heats and vaporizes the sterilizer sprayed into the pipe. The gas of the vaporized sterilizer blasts from the sterilizer gas blasting nozzle 31 to the outside of the vaporizing portion 57. The vaporizing portion 57 may be heated by dielectric heating instead of the heater 57a.

As the operating conditions of the sterilizer supplying portion 56, for example, the pressure of the compressed air is adjusted in a range of 0.05 MPa to 0.6 MPa. Further, the sterilizer may be dropped by gravity or may be applied with pressure, and the supply amount thereof can be freely set. For example, the sterilizer is supplied to the sterilizer supply path 56a in a range of 1 g/min. to 100 g/min. Further, the inner surface of the vaporizing portion 57 is heated to from 140° C. to 450° C., and thereby the sprayed sterilizer vaporizes.

The gas of the sterilizer is blasted from the sterilizer gas blasting nozzle 31 onto the container 2 as shown in FIG. 3(E). The blasting amount of the gas or mist, or a mixture thereof, of the sterilizer is arbitrary, but the blasting amount is determined by the amount and the blasting time of the sterilizer supplied to the sterilizer gas generator 55. There may be provided a plurality of sterilizer gas generators 55. The blasting amount may vary depending on the size of the container 2.

It is preferable that the sterilizer at least contains hydrogen peroxide. An appropriate content thereof is in a range of 0.5 mass % to 65 mass %. If it is less than 0.5 mass %, the sterilizing power may be insufficient, and if it is more than 65 mass %, handling becomes difficult for safety reasons. More preferably, the content is 0.5 mass % to 40 mass %, and when it is 40 mass % or less, handling becomes easier and, due to low concentration, the residual amount of the sterilizer in the container 2 after sterilization can be reduced.

When the sterilizer is a hydrogen peroxide solution, the blasting amount of the gas of a hydrogen peroxide solution is as follows. The amount of hydrogen peroxide adhering to the inner surface of the container 2 due to the gas of the hydrogen peroxide solution blasted from the sterilizer gas blasting nozzle 31 onto the inner surface of the container 2 is preferably 30 μL/container to 150 μL/container, and more preferably 50 μL/container to 100 μL/container in the amount of a hydrogen peroxide solution containing 35 mass % of hydrogen peroxide. The hydrogen peroxide concentration of the gas of the hydrogen peroxide solution which is blasted onto the container 2 is preferably 2 mg/L to 20 mg/L, and more preferably 5 mg/L to 10 mg/L.

While the sterilizer contains water, it may contain one or more kinds of alcohols such as methyl alcohol, ethyl alcohol, isopropyl alcohol, normal propyl alcohol, and butyl alcohol, ketones such as acetone, methyl ethyl ketone, and acetyl acetone, glycol ethers, and the like.

Further, the sterilizer may include additives, such as organic acids such as peracetic acid and acetic acid, chlorine compounds such as sodium hypochlorite, compounds having a sterilizing effect such as ozone, cationic surfactants, nonionic surfactants, phosphoric acid compounds, and the like.

As shown in FIG. 1, the container 2 sterilized by the container sterilizing portion 30 is conveyed to the air rinsing portion 34 via the wheel 29. In the air rinsing wheel 35 shown in FIG. 1, aseptic air is blasted onto the container 2 in an upright state by the air rinsing nozzle 38 as shown in FIG. 3(F-1). Aseptic air may be at room temperature, but is preferably heated. The aseptic air also has effects of discharging the sterilizer remaining in the inside of the container 2, decomposing the remaining sterilizer to further enhance sterilizing effect, and removing foreign matters when they are present in the inside of the container 2. Further, aseptic air may be blasted onto the interior of the container 2 with the container 2 brought into an inverted state as shown in FIG. 3(F-2). In this state, removing foreign matters is more effective than in an upright state. Further, similarly to the sterilizer blasting nozzle 31 shown in FIG. 3(E-2), by providing a guide member surrounding the air rinsing nozzle 38, aseptic air that is introduced into the container 2 and overflows from the mouth portion 1a collides with the guide member, thereby also rinsing the outer peripheral portion of the mouth portion 1a so that the temperature of the outer peripheral portion of the mouth portion 1a increases, and the sterilizing effect of the outer peripheral portion of the mouth portion 1a is enhanced. The air rinsing nozzle 38 may be configured to be movable in an up and down direction such that aseptic air is blown into the container 2.

As shown in FIG. 1, the container 2 that has been air rinsed by the air rinsing portion 34 is conveyed to the filling portion 39 via the wheel 37. At the filling portion 39, in the filling wheel 40 shown in FIG. 1, the container 2 is filled with a content by the filling nozzle 42 as in the filling step shown in FIG. 3(G). The content is sterilized in advance, and a fixed amount of the content such as a drink is filled in the container 2 by the filling nozzle 42 travelling in synchronous with the container 2.

Figure 6:
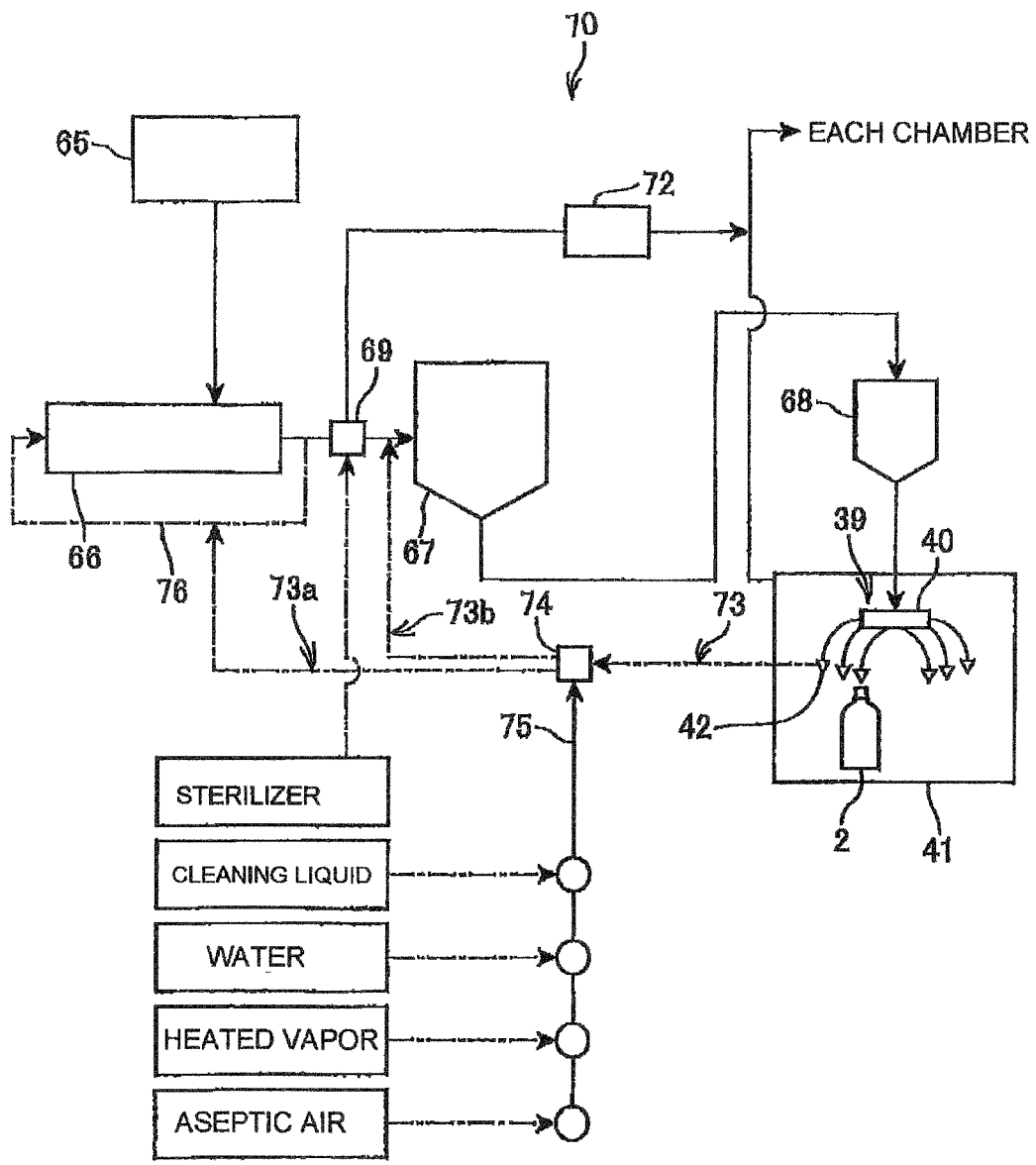
FIG. 6 is a diagram showing a content sterilization apparatus and an aseptic water supply apparatus, which are included in the aseptic filler according to Embodiment of the present invention.

As shown in FIG. 6, the aseptic filler includes a preparation apparatus 65 of content and a content sterilization apparatus 66 for sterilizing the content, and the content sterilization apparatus 66 and the filling nozzle 42 of the filling portion 39 are connected by content supply piping.

The preparation apparatus 65 is for preparing drinks, for example, tea drinks and fruit drinks at desired blending ratios, but since it is a known apparatus, detailed description thereof will be omitted.

The filling portion 39, which is formed by arranging a large number of filling nozzles 42 around a filling wheel 40 that rotates at a high speed in a horizontal plane, fills the container 2, which travels beneath the filling nozzle 42 in conformity with the circumferential speed of the filling wheel 40, with the drink from the filling nozzle 42 by a predetermined amount, while rotating the filling nozzle 42 with the rotation of the filling wheel 40.

The content sterilization apparatus 66 is an apparatus that heats the content from 20° C. to 65° C. by a first stage heating portion which is formed by linking multiple shell-and-tube type heat exchangers in series; heats the content from 65° C. to 140° C. by a second stage heating portion which is formed by linking in series a larger number of shell-and-tube type heat exchangers than in the first stage heating portion; and holds and sterilizes the content, which is heated to 140° C., at 140° C., with a holding tube. The content is further cooled to a room temperature by a cooling portion provided in the content sterilization apparatus 66.

The content, which is prepared in the preparation apparatus 65 and sterilized in the content sterilization apparatus 66 is stored into a surge tank 67 via a switching valve 69, is further fed to a head tank 68 provided in the vicinity of the filling portion 39, and is supplied from the head tank 68 to the filling nozzle 42 to be filled in the container 2.

The container 2 filled with the content is conveyed to the sealing portion 44 via a wheel 43 shown in FIG. 1. In the sealing wheel 45 provided in the sealing portion 44, like the sealing step as shown in FIG. 3(H), a lid material 3 which is a sealing member sterilized by the lid-material sterilizing portion 52 is supplied to a sealing wheel 45 via a lid material supply wheel 54a and a lid material receiving wheel 54b by a sterilized lid-material conveying path 54, and is wound up onto the mouth portion 1a of the container 2 by a capper not shown, thereby sealing the container 2.

The sealed container 2 is passed to the gripper 22 of the discharge wheel 48 of the discharging portion 47 from the gripper 22 of the sealing wheel 45. The container 2 that has been passed to the discharge wheel 48 is placed on the discharging conveyor 50. The container 2 placed on the discharging conveyor 50 is discharged from inside of the outlet portion chamber 53 to the outside of the aseptic filler.

Figure 5:
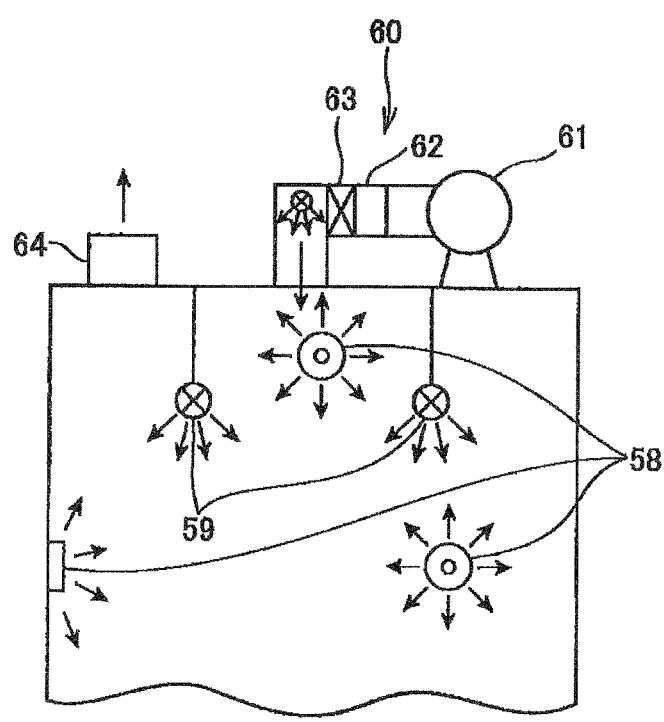
FIG. 5 is a diagram showing a sterilizer blasting nozzle, a liquid blasting nozzle, and an aseptic air supply apparatus, which are incorporated in the chambers of the aseptic filler according to Embodiment 1 of the present invention.

Interiors of the container sterilizing portion chamber 33, the air rinsing portion chamber 36, the filling portion chamber 41, the sealing portion chamber 46, the discharging portion chamber 49, and the outlet portion chamber 53 are subjected to the SOP treatment before operation of the aseptic filler. For that reason, as shown in FIG. 5, each chamber includes a sterilizer spraying nozzle 58 and a liquid spraying nozzle 59. As described above, the container sterilizing portion chamber 33 may not be subjected to the SOP treatment.

The sterilizer spraying nozzle 58 uses a one-fluid spray or a twin-fluid spray that mixes and sprays the sterilizer with compressed air, and the sterilizer is sprayed so as to adhere to the entire area in each chamber that requires sterilization. The interior of each chamber is sterilized by the sprayed sterilizer. The sterilizer spraying nozzle 58 is arranged such that the sterilizer adheres to the entire area of the interior of each chamber. As the sterilizer, the same sterilizer as that used for sterilizing the container 2 can be used, and it is preferable to use a sterilizer containing peracetic acid or hydrogen peroxide. The spraying of the sterilizer may be performed by spraying different sterilizers multiple times.

When peracetic acid is contained as a sterilizer, the peracetic acid concentration is 500 ppm or more, and preferably 1000 ppm or more. In this case of the sterilization condition, the sterilizer is heated to 40° C. to 95° C., and preferably 50° C. to 95° C., and the sterilizer is sprayed into the chamber such that not less than 0.01 g/cm², preferably not less than 0.1 g/cm² of peracetic acid adheres onto the surfaces of the apparatus and the wall in the chamber. The spraying time is preferably 30 seconds to 30 minutes. The spraying may be performed for 30 minutes or more, but the productivity will be reduced.

After the sterilizer is sprayed from the sterilizer spraying nozzle 58, aseptic water is sprayed onto the entire area of the interior of each chamber by the liquid spraying nozzle 59. With this aseptic water, sterilizer remaining in each chamber is cleaned. The liquid nozzle spraying 59 is arranged such that the liquid is sprayed onto the entire area of the interior of each chamber. The aseptic water is water which is sterilized by being heated at 121.1° C. or more, for 4 minutes or more, by the content sterilization apparatus 66. The aseptic water which is sprayed onto the interior of each chamber from the liquid spraying nozzle 59 is preferably heated at 20° C. to 100° C., and more preferably at 60° C. to 100° C. Heating at 60° C. or more will increase cleaning ability of the aseptic water. Moreover, heating at more than 100° C. may damage the liquid spraying nozzle 59, and is therefore not preferable. Moreover, part of the aseptic water to be supplied may vaporize and cause pulsation, resulting in unstable supply. As the liquid spraying nozzle 59, for example, a spray nozzle using a spin ball is used. Aseptic water may be sprayed from the sterilizer spraying nozzle 58 without providing the liquid spraying nozzle 59. In order to perform efficient cleaning in a short time, it is preferable to supply aseptic water to the liquid spraying nozzle 59 at a liquid feeding pressure of 0.1 MPa or more, and preferably 0.2 MPa or more. After cleaning the interior of each chamber with aseptic water, the aseptic water is discharged from inside the chamber. It is preferable that the non-aseptic area from which aseptic water is discharged and the interior of each chamber are sealed from each other with a water sealing mechanism. Further, the sterilizer n spraying ozzle 58 and the liquid spraying nozzle 59 are preferably attached at positions away from the conveying path above the mouth portion of the container 2 in order to avoid the risk of contamination into the container 2.

Since the content of the filling portion chamber 41 are scattered in the chamber and are heavily contaminated, a SOP treatment using a sterilizer such as peracetic acid, or an alkaline solution mainly composed of caustic soda as the sterilizer is performed. However, since the discharging portion chamber 49 and the outlet portion chamber 53 are limited in contamination, a SOP treatment using only hydrogen peroxide may be performed and, in this case, cleaning with aseptic water may not be performed. Therefore, the aseptic water produced by the content sterilization apparatus 66 is supplied at least to the filling portion chamber 41. Therefore, an aseptic water supply apparatus 70 that supplies aseptic water produced by the content sterilization apparatus 66 is provided at least in the filling portion chamber 41.

If the interior of the sealing portion chamber 46 is also contaminated with the content, a SOP treatment using a sterilizer such as peracetic acid or an alkaline solution mainly composed of caustic soda is performed. Therefore, aseptic water produced by the content sterilization apparatus 66 is also supplied to the interior of the sealing portion chamber 46.

Aseptic water is produced by supplying water to the content sterilization apparatus 66 and sterilizing by heating the supplied water with the content sterilization apparatus 66. As shown in FIG. 6, the produced aseptic water is supplied to the filling portion chamber 41 by the aseptic water supply apparatus 70 via the switching valve 69, and is sprayed onto the interior of the chamber from the liquid spraying nozzle 59. Further, it may be supplied to a chamber other than the filling portion chamber 41. Aseptic water is produced by heating the water by the content sterilization apparatus 66, but since it is cooled by the content sterilization apparatus 66, the aseptic water is preferably heated in order to improve the cleaning ability of the aseptic water supplied into each chamber. Therefore, the aseptic water is heated by a heater 72 before it is supplied to the filling portion chamber 41 and each chamber via the switching valve 69. Aseptic water is preferably heated to 60° C. to 100° C. as described above.

Figure 7:
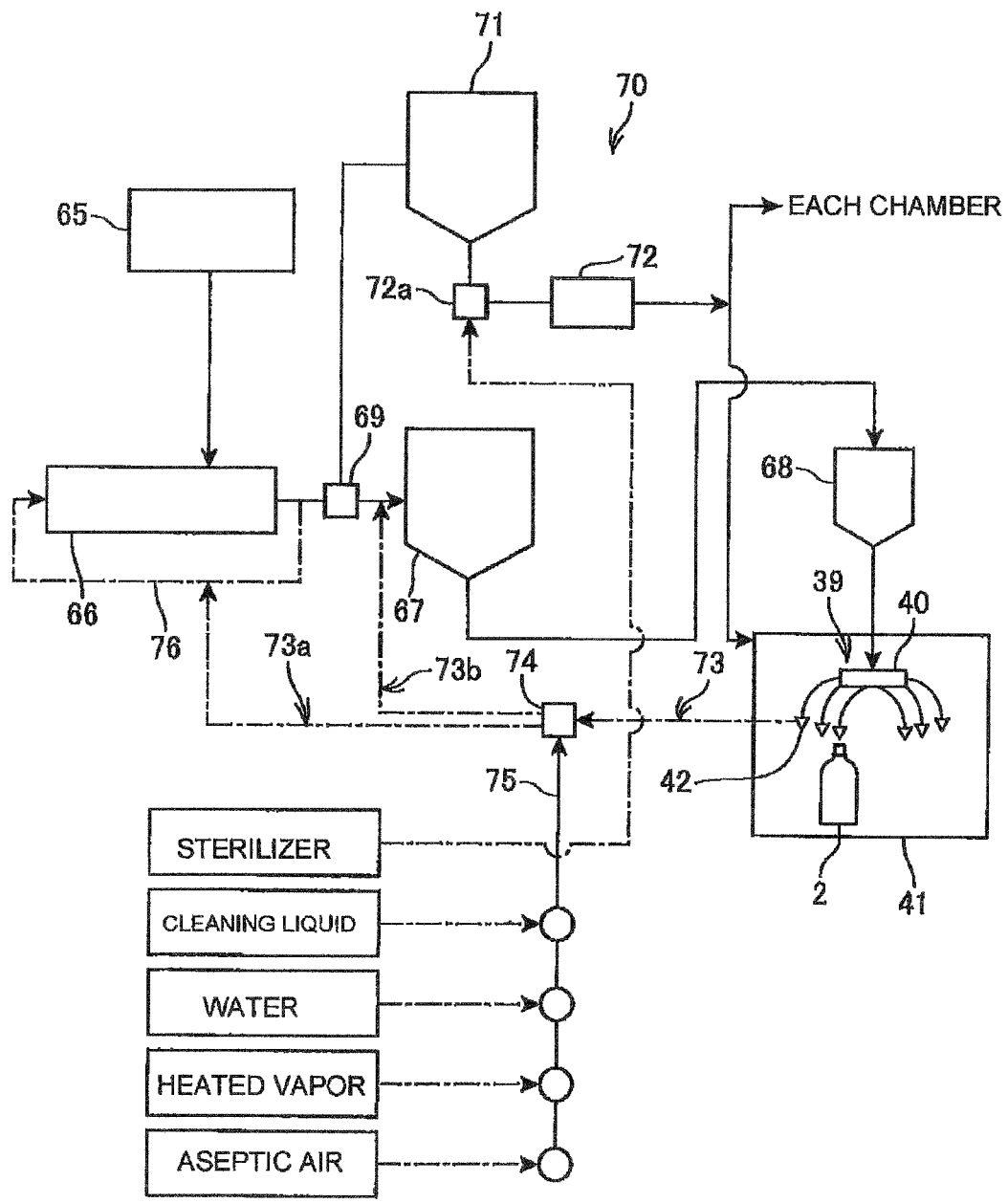
FIG. 7 is a diagram showing a content sterilization apparatus and an aseptic water supply apparatus including an aseptic water reservoir tank, which are included in the aseptic filler according to Embodiment of the present invention.

Further, as shown in FIG. 7, aseptic water may be supplied to each chamber after being stored in the aseptic water reservoir tank 71. The aseptic water supply apparatus 70 includes aseptic water supply piping from the switching valve 69 to each chamber, the aseptic water reservoir tank 71, and the heater 72. Further, the aseptic water supply apparatus 70 may include an aseptic air supply apparatus that supplies aseptic air in order to pump aseptic water.

Further, the aseptic water supply apparatus 70 may include an aseptic-type pump provided with a steam barrier for supplying aseptic water to each chamber. The supply of aseptic water to each chamber may be performed to a single chamber or to a plurality of chambers at the same time.

Before supplying aseptic water to each chamber, the interior of the aseptic water supply piping is sterilized. As shown in FIG. 6, the piping from the switching valve 69 to each chamber is preferably sterilized with a sterilizer (mainly peracetic acid or hydrogen peroxide) before feeding aseptic water. This is because sterilization with heated steam is not preferable since the liquid spraying nozzle 59 may be damaged by heat.

When sterilizing the interior of the aseptic water supply piping, which supplies aseptic water into each chamber, with a sterilizer mainly composed of peracetic acid, this is done by feeding the sterilizer having a peracetic acid concentration of 500 ppm or more, and preferably 1000 ppm to 5000 ppm to the interior of the aseptic water supply piping. At this time, the sterilizer is heated to 40° C. to 95° C., and preferably 50° C. to 95° C., and is liquid fed at 1.0 m/sec or more of flow velocity in the piping. The liquid feeding time is preferably 30 seconds to 30 minutes. The peracetic acid concentration of the sterilizer may be set to 5000 ppm or more, or liquid feeding of the sterilizer may be performed for 30 minutes or more, but the cost increases and the productivity decreases.

When sterilizing the interior of aseptic water supply piping with a sterilizer mainly composed of hydrogen peroxide, it is possible to sterilize the interior of the aseptic water supply piping by supplying aseptic air which contains hydrogen peroxide at a concentration of 1.0 to 20 mg/L at a temperature of 50 to 100° C., to the interior of the aseptic water supply piping for 5 minutes or more. Supplying aseptic air containing hydrogen peroxide at a concentration of 20 mg/L or more will result in cost increase and productivity decrease.

The sterilization in the aseptic water supply piping may be sterilized with both a sterilizer mainly composed of peracetic acid and a sterilizer mainly composed of hydrogen peroxide. In that case, it is preferable to first perform sterilization with a sterilizer mainly composed of peracetic acid, and thereafter perform sterilization with a sterilizer mainly composed of hydrogen peroxide, which has a high sterilizing effect.

As shown in FIG. 7, when the aseptic water supply apparatus 70 includes the aseptic water reservoir tank 71, sterilization by the sterilizer in the aseptic water supply piping is performed by supplying the sterilizer to the switching valve 72a in the upstream of the heater 72, and sterilizing the aseptic water supply piping extending from the switching valve 72a to each chamber via the heater 72. Sterilization of the inside of the aseptic water supply piping extending from the switching valve 69 to the switching valve 72a is preferably performed by heated steam. This is because when a sterilizer is used to sterilize the aseptic water reservoir tank 71, the amount of the sterilizer used will significantly increase.

As shown in FIG. 7, by providing the aseptic water reservoir tank 71, it is possible to produce and store aseptic water by the content sterilization apparatus 66, when the CIP treatment or SIP treatment in the content supply piping that supplies the content to the filling portion 41 is being performed, after the CIP treatment and the SIP treatment of the content sterilization apparatus 66, which are performed when the content is changed, is ended. Among the container sterilizing portion chamber 33 that supplies aseptic water, the air rinsing portion chamber 36, the filling portion chamber 41, the sealing portion chamber 46, the discharging portion chamber 49 and the outlet portion chamber 53, the filling portion chamber 41 is a relatively large chamber, and the amount of aseptic water to be supplied thereto is large. Therefore, there is a case in which aseptic water runs short when aseptic water is supplied while being produced by the content sterilization apparatus 66. By using the aseptic water to be stored in the reservoir tank 71, it is possible to supply a required amount of aseptic water to the filling portion chamber 41 and other chambers, and complete the SOP treatment of each chamber in a short time.

Figure 8:
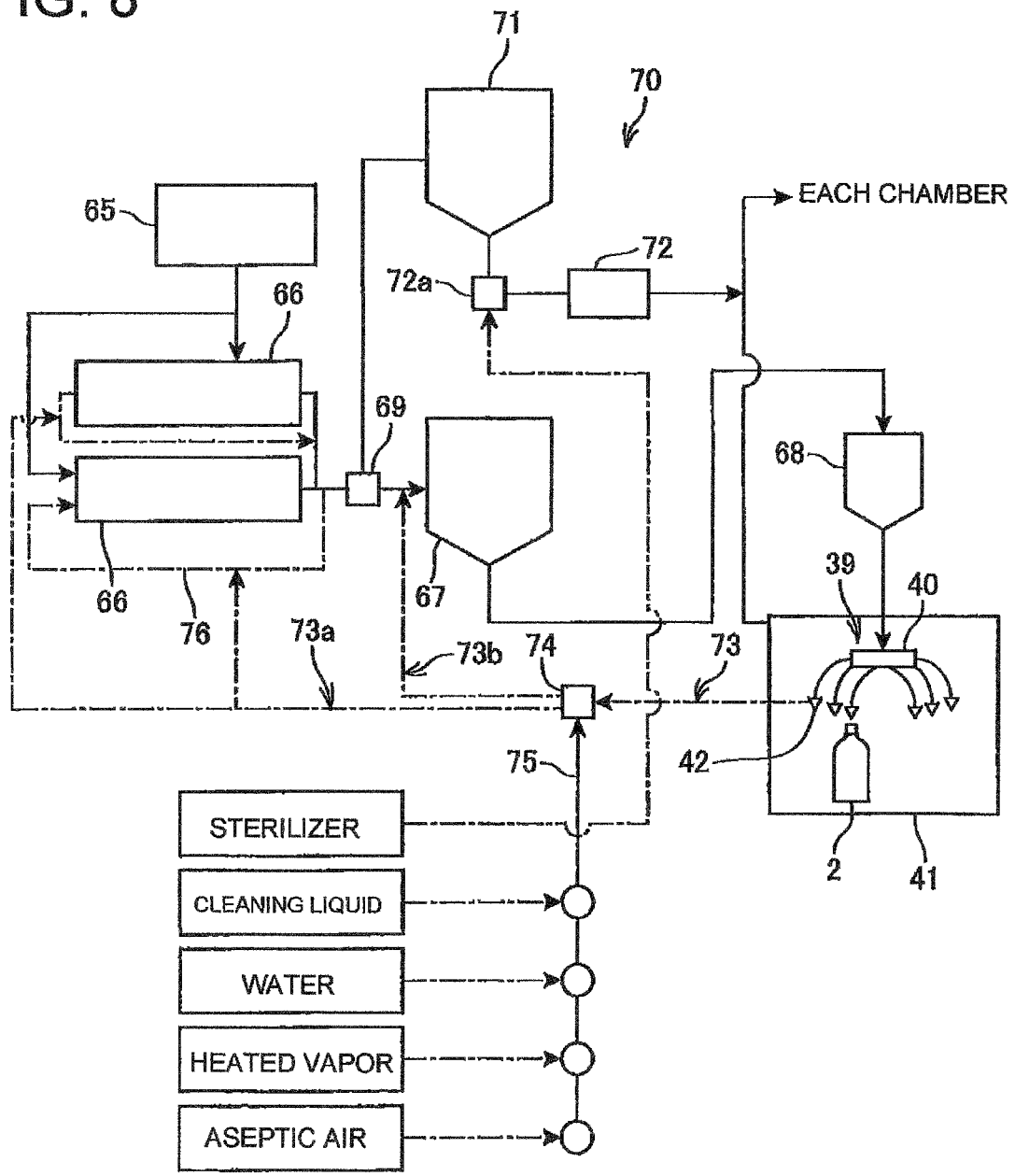
FIG. 8 is a diagram showing a plurality of content sterilization apparatuses and an aseptic water supply apparatus, which are provided in the aseptic filler according to Embodiment of the present invention.

As shown in FIG. 8, a plurality of the content sterilization apparatuses 66 may be provided. The purpose of providing a plurality of the content sterilization apparatuses 66 is for reducing the changing time of different contents. A part of the content sterilization apparatus 66, which is subject to a relatively high temperature, may cause scorching depending on the content so that it may take a long time for the CIP treatment of the content sterilization apparatus 66 when changing the content. At this time, by providing a plurality of content sterilization apparatuses 66, and arranging such that when the content is sterilized and filled by one of the content sterilization apparatuses 66, the CIP treatment and SIP treatment of another of the content sterilization apparatuses 66 are completed, it is possible to sterilize and fill the next content by instantly using another of the content sterilization apparatuses 66 when changing the content. After completing the CIP treatment and SIP treatment of another of the content sterilization apparatuses 66, it is possible to produce aseptic water and store the aseptic water in the aseptic water reservoir tank 71, and it is also possible to immediately perform aseptic water supply to each chamber when each chamber needs aseptic water.

While aseptic water supplied to each chamber is at 20° C. to 100° C., and preferably at 60° C. to 100° C., this is achieved by supplying the aseptic water, which has been sterilized by heating in the content sterilization apparatus 66, to each chamber in a state of being cooled to 60° C. to 100° C. without being cooled to the room temperature. At this time, there is no need of heating the aseptic water with a heater 72. By setting the temperature of the aseptic water to 60° C. or more, in addition to improving the cleaning ability, a sterilizing effect by the warmed aseptic water is expected against heat-resistant fungi and heat-resistant yeast, which have been damaged by chemical agents such as peracetic acid and alkali, which are sterilizers used for the SOP treatment.

It is also possible to sterilize nutrient cells of fungi, yeast, and bacteria, other than bacterial spores by setting the temperature of aseptic water to 60° C. to 100° C. without using a sterilizer such as peracetic acid or an alkaline solution. Since the cleaning effect is high when the temperature of aseptic water is 60° C. or more, sterilization and cleaning can be performed simultaneously in one step. Simultaneous sterilization and cleaning with warmed aseptic water is effective as the SOP treatment for an aseptic filler including an acidic drink or mineral water as the content. The SOP treatment with heated aseptic water may be performed in the molding portion chamber 17 and the lid-material sterilizing portion 52 other than the filling portion chamber 41 and the sealing portion chamber 46 in which the product liquid is scattered.

While aseptic water is sprayed to the interior of each chamber after the sterilizer is sprayed, when, before the sterilizer is sprayed, the content is scattered in the filling portion chamber 41, the sealing portion chamber 46, the discharging portion chamber 49 and the outlet portion chamber 53, a cleaning liquid is sprayed from the liquid spraying nozzle 59, and the interior of each chamber is subjected to the COP treatment. The cleaning liquid is water, or water containing an acidic compound or a basic compound. The water may be any water that does not contain foreign matters, such as ion-exchanged water, distilled water, and tap water. The acidic compound is an inorganic acid such as hydrochloric acid, nitric acid, and phosphoric acid, or an organic acid such as acetic acid, formic acid, octanoic acid, oxalic acid, citric acid, succinic acid, and gluconic acid. The basic compound is an inorganic basic compound such as sodium hydroxide and potassium hydroxide, or an organic basic compound such as ethanolamine and diethylamine. In addition to that, metal-ion blocking agents such as alkali metal salts, alkaline earth metal salts, ammonium salts of organic acids, and ethylenediamine tetraacetic acid, anionic surfactants, cationic surfactants, nonionic surfactants such as polyoxyethylene alkylphenyl ethers, solubilizers such as sodium cumenesulfonate, acid-based polymers such as polyacrylic acid or metal salts thereof, corrosion inhibitors, preservatives, antioxidants, dispersants, defoaming agents, etc. may be contained. Further, since these cleaning liquids also have a sterilizing action when heated to 50° C. or more, the cleaning liquids may be used as a sterilizer for sterilizing the interior of the chamber.

Each chamber is equipped with an aseptic air supply apparatus 60, as shown in FIG. 5. The aseptic air supply apparatus 60 is connected to an upper portion of each chamber. The aseptic air supply apparatus 60 includes a blower 61, a heating apparatus 62, and an aseptic filter 63. The air from the blower 61 is heated by the heating apparatus 62, filtered by the aseptic filter 63, and thereafter becomes aseptic air to be supplied into each chamber. As shown in FIG. 5, the aseptic filter 63 is provided perpendicular to the top surface of the chamber, this is in order to prevent the cleaning liquid and the sterilizer from adhering to the surface of the aseptic filter 63. The aseptic filter 63 may be provided parallel to the chamber surface.

Moreover, each chamber is equipped with an exhaust apparatus 64, which operates together with the aseptic air supply apparatus 60 to keep the pressure inside each chamber at an appropriate value.

The aseptic water sprayed from the liquid spraying nozzle 59 and remaining in each chamber is vaporized and removed by the aseptic air supplied from the aseptic air supply apparatus 60. At this time, when the aseptic air is heated, removal of the aseptic water by vaporization is quickly performed. Further, the aseptic air supply apparatus 60 supplies aseptic air into each chamber in order to maintain the aseptic condition in each chamber during operation of the aseptic filler. In this case, the aseptic air may not be heated.

It is preferable to dry the interior of each chamber as much as possible before sterilizing the interior of each chamber with a sterilizer mainly composed of hydrogen peroxide. In a wet state, hydrogen peroxide dissolves into the liquid and the concentration of hydrogen peroxide existing as a gas decreases so that the sterilizing ability cannot be exhibited. In order to efficiently remove the aseptic water remaining in each chamber in a short time, it is preferable to rotate the wheel in each chamber. When the CIP treatment or SIP treatment of the filling portion 39 is being performed, the clutch of the wheel of the filling wheel 40 is disengaged to rotate the wheels other than the filling wheel 40. The rotation speed may be increased to the operating speed at the time of production. By the centrifugal force generated by this high-speed rotation, it is possible to remove the aseptic water adhering to the wheels other than the filling wheel 40, such as the sealing wheel 45, the air rinsing wheel 35, and the wheel 28, the gripper 22, and a bellows of each portion in the aseptic filler. This residual water removing step is performed while supplying aseptic air such that the aseptic condition does not deteriorate. It is preferable that removal of the residual water of the filling portion 39 is performed after ending of the CIP treatment of the filling portion 39 and before the SOP treatment.

In sterilization before operation of the aseptic filler, the surface of the aseptic filter 63 can also be sterilized by a sterilizer sprayed with the sterilizer spraying nozzle 58. The surface of the aseptic filter 63 may be sterilized with a gas or mist, or a mixture thereof, of a hydrogen peroxide solution.

The content supply piping extending from the content sterilization apparatus 66 to the filling nozzle 42 is subjected to the CIP treatment and the SIP treatment when changing the content. These may be performed simultaneously with the COP treatment and the SOP treatment, or performed sequentially.

As shown in FIG. 6, a circulation pipe line 73 for circulating a cleaning liquid for the CIP treatment, which is discharged from the filling nozzle 42, is provided. The connection between the filling nozzle 42 and the circulation pipe line 73 is, although not shown, is performed by a cup provided in the circulation pipe line 73 being placed on the tip of the filling nozzle 42 by an actuator.

An introduction pipe 75 for supplying the cleaning liquid or the like to the circulation pipe line 73 is connected to the circulation pipe line 73 via a valve manifold 74. Supply sources of cleaning liquid, water, heated steam, and aseptic air are connected to the upstream side of the introduction pipe 75 via switching valves, respectively. Various other types of valves, pumps, and the like are provided in the circulation pipe line 73 and the introduction pipe 75, but the illustration thereof is omitted. There are provided a circulation pipe line 73a connected from the valve manifold 74 to the outlet of the content sterilization apparatus 66 and a circulation pipe line 73b to be connected to the upstream of the surge tank 67. Further, a sterilization apparatus circulation path 76 is provided in the circulation pipe line 73a. That is, a circulation path extending from the surge tank 67 and the head tank 68 to the filling nozzle 42 through the circulation path 76 that circulates in the content sterilization apparatus 66, and the circulation pipe line 73 and 73b are formed. A cleaning liquid and water is supplied from the introduction pipe 75 to these circulation paths and circulated to perform the CIP treatment. The cleaning liquid and water may be the same as those used for the COP treatment.

Further, the SIP treatment is performed by supplying heated steam to the content supply piping. The heated steam to be used for the SIP treatment is blown out from the filling nozzle 42 to perform the SIP treatment in the content supply piping. After the SIP treatment, aseptic air is introduced into the content supply piping to maintain an aseptic condition in the content supply piping.

While Embodiment 1 is an aseptic filler that sterilizes the container 2, the preform 1 may be sterilized before the container 2 is sterilized.

Embodiment 2

Figure 9:
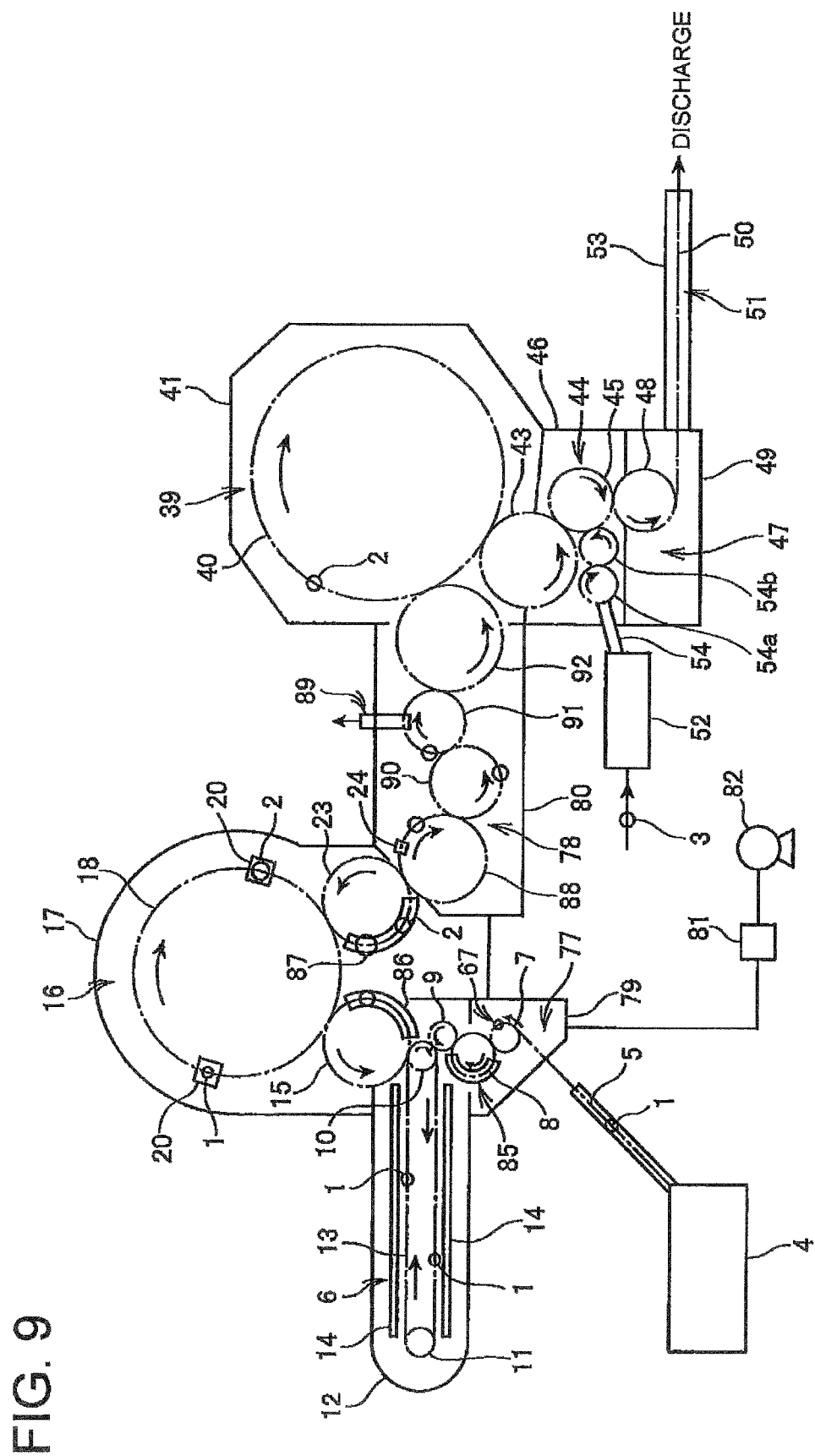
FIG. 9 is a plan view showing an outline of an aseptic filler according to Embodiment 2 of the present invention.

FIG. 9 shows Embodiment 2 of the present invention. While Embodiment 1 is an aseptic filler that sterilizes a container 2, Embodiment 2 is an aseptic filler that sterilizes a preform 1 and does not sterilize the container 2. Hereinafter, an aseptic filler including a preform sterilizing portion 77 that sterilizes the preform 1 will be described.

Outline of Embodiment 2

As shown in FIG. 9, an aseptic filler according to Embodiment 2 includes: a preform supply apparatus 4 that supplies a preform 1; a preform sterilizing portion 77 that sterilizes the preform 1; a heating portion 6 that heats the preform 1 to a temperature for molding the same into a container 2; a molding portion 16 that molds the heated preform 1 into the container 2; an inspecting portion 78 that inspects the formed container 2; a filling portion 39 that fills the container 2, which has been determined to be normal by the inspection, with the sterilized content; a lid-material sterilizing portion 52 that sterilizes a lid material 3 which is a sealing member; a sealing portion 44 that seals the container 2, which is filled with the content, with the sterilized lid material 3; a discharging portion 47 that places the sealed container 2 on a discharging conveyor 50; and an outlet portion 51 that discharges the container 2 to a non-aseptic zone by the discharging conveyor 50. The inspecting portion 78 may not be included.

The preform sterilizing portion 77 is shielded by a preform sterilizing portion chamber 79; the heating portion 6 by a heating portion chamber 12; the molding portion 16 by a molding portion chamber 17; the inspecting portion 78 by an inspecting portion chamber 80; the filling portion 39 by a filling portion chamber 41; the sealing portion 44 by a sealing portion chamber 46; the discharging portion 47 by a discharging portion chamber 49; and the outlet portion 51 by an outlet portion chamber 53. Unlike Embodiment 1, the molding portion 16 and the inspecting portion 78 may not be in the same chamber, and may be shielded by the molding portion chamber 17 and the inspecting portion chamber 80, respectively. Here, the lid-material sterilizing portion 52 and the sealing portion 44 may be shielded by a single chamber. Further, the sealing portion 44 and the discharging portion 47 may also be shielded by a single chamber.

Aseptic air, which is sterilized by an aseptic filter during operation of the aseptic filler, is supplied to the heating portion chamber 12, the molding portion chamber 17, the inspecting portion chamber 80, the filling portion chamber 41, the sealing portion chamber 46, the discharging portion chamber 49, and the outlet portion chamber 53, so that the aseptic condition of the aseptic filler is maintained by making the pressure inside each chamber positive. The pressure to be made positive is set highest in the filling portion chamber 41 and lower toward the upstream or downstream. For example, when the pressure in the filling portion chamber 41 is 20 Pa to 40 Pa, the pressure in the other chambers is lower than the pressure in the filling portion chamber 41.

The preform sterilizing portion chamber 79 is linked to an exhaustion device including a filter 81 that decomposes a sterilizer in the air in the preform sterilizing portion chamber 79 and a blower 82. By exhausting the air in the preform sterilizing portion chamber 79 during the operation of the aseptic filler, it is possible to prevent the sterilizer from flowing into the adjacent heating portion 6. Therefore, during the operation of the aseptic filler, the pressure in the preform sterilizing portion chamber 79 is substantially equal to, or negative to the atmospheric pressure.

Details of Embodiment 2

By the preform supply apparatus 4 shown in FIG. 9, the preform 1 is continuously conveyed to the preform steriliz-ing portion 77 at a desired speed by the preform supply conveyor 5. The preform 1 is the same as one of Embodiment 1.

Figure 10J:
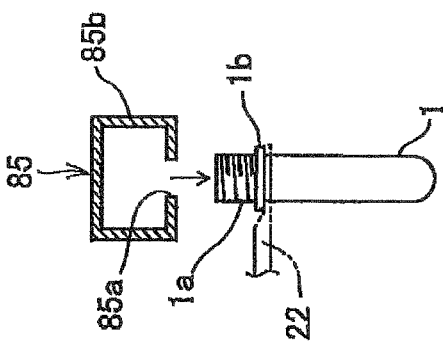
FIG. 10 is a diagram showing the process step of a preform sterilizing portion of the aseptic filler according to Embodiment 2 of the present invention, in which (I) shows a sterilizer gas blasting step to a preform, and (J) an air blasting step to the preform.
Figure 10I:
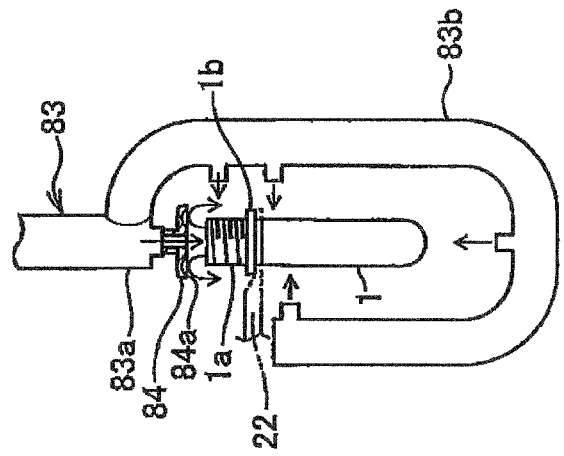

The preform 1 is gripped by grippers 22 provided on the wheel 7 at regular intervals from the preform supply conveyor 5, and a gas or mist, or a mixture thereof, of the sterilizer is blasted by a preform sterilizer gas blasting nozzle 83 provided on the wheel 7 as shown in FIG. 10(I).

As shown in FIG. 10 (I), a gas or mist, or a mixture thereof, of the sterilizer flows in two ways in the preform sterilizer gas blasting nozzle 83, and is blasted toward the inside of the preform 1 from one of the nozzles 83a, and is blasted toward the outer surface of the preform 1 from the other nozzle 83b. The gas or mist, or a mixture thereof, of the sterilizer exits the preform sterilizer gas blasting nozzle 83, and then flows into the inside of the preform 1 in a gas state, or as a mist or a mixture thereof. Alternatively, it comes into contact with the outer surface of the preform 1.

While a gas or mist, or a mixture thereof, of the sterilizer, which is blasted toward the inside of the preform 1, flows into the preform 1, and thereafter overflows from the mouth portion 1a of the preform 1, the flow of the overflown gas or mist, or a mixture thereof, of the sterilizer collides with a guide member 84 and is guided by the inner surface of the guide member 84 so that the flow is changed toward the outer surface of the preform 1 to come into contact with the outer surface of the preform 1. When the guide member 84 is provided with an annular groove 84a, the overflowing gas or mist, or a mixture thereof, of the sterilizer flows along the outer surface of the preform 1.

In this way, the gas or mist or a mixture thereof of the sterilizer comes into contact with and adheres to the inner and outer surfaces of the preform 1 so that the bacteria and the like adhering to the surface of the preform 1 are sterilized.

Not only one preform sterilizer gas blasting nozzle 83 shown in FIG. 10(I), but also a plurality of them may be arranged along the traveling path of the preform 1 so as to blast the gas or mist, or a mixture thereof, of the sterilizer from these preform sterilizer gas blasting nozzles 83 toward the preform 1. Further, by changing the diameter of the preform-sterilizer gas blasting nozzle 83, the nozzle 83a, or the nozzle 83b, or the diameter and the number of sterilizer gas blow-out openings provided in the nozzle 83b, it is possible to adjust the adhering amount of the sterilizer onto the inner surface and the outer surface of the preform 1, respectively.

Note that room temperature aseptic air, or heated aseptic air may be supplied to the preform sterilizer gas blasting nozzle 83, the nozzle 83a, and the nozzle 83b from the middle of these such that a gas or mist, or a mixture thereof, of the sterilizer, which is diluted with aseptic air, is blasted to the preform 1.

Note that the preform 1 may be preheated, for example by blasting hot air on the preform 1 immediately before blasting the gas of the sterilizer onto the preform 1 shown in FIG. 10(I). This preheating can further enhance the effect of sterilizing the preform 1.

A sterilizer similar to that of Embodiment 1 is used. Further, gasification of the sterilizer is carried out by a sterilizer gas generator 55 similar to that of Embodiment 1. The blasting amount of gas of the sterilizer is arbitrary, but when the sterilizer is a hydrogen peroxide solution, the adhering amount of hydrogen peroxide to the preform 1 is preferably 0.001 µL/cm$^2$ to 0.5 µL/cm$^2$ in the amount of hydrogen peroxide solution containing 35 mass % of hydrogen peroxide. When the adhering amount is less than 0.001

µL/cm², sufficient sterilizing effect cannot be achieved. Further, if the adhering amount is more than 0.5 µL/cm², when the preform 1 is blow molded into the container 2, molding defects such as whitening, spotting, wrinkles, and deformation occur in the container 2, and the amount of hydrogen peroxide remaining in the container 2 increases.

The preform 1 which has been blasted with the gas of the sterilizer may be blasted with aseptic air by the air blasting nozzle 85 while being grasped by the gripper 22 and conveyed, as shown in FIG. 10(J). Depending on the type and the amount of the sterilizer, blasting of aseptic air may not be performed.

By the blasting of aseptic air, the sterilizer adhering to the surface of the preform 1 is activated, and bacteria and the like on the inner and outer surfaces of the preform 1 are sterilized. Further, by the blasting of aseptic air, the sterilizer adhering to the preform 1 is quickly removed from the surface of the preform 1. The sterilizer adhering to the preform 1 is removed from the preform 1 by the blasting of aseptic air before heating. In addition, foreign matters in the preform 1 are also removed by the blasting of aseptic air onto the preform 1.

Aseptic air may be at room temperature, but by heating it to obtain aseptic hot air, its sterilizing effect is enhanced, and when the sterilizer contains hydrogen peroxide, the amount of hydrogen peroxide remaining in the preform 1 also decreases. Heating of the aseptic air is preferably performed such that the temperature of the aseptic hot air blasted onto the preform 1 is 40° C. to 140° C. If the temperature is less than 40° C., the effect by heating is small, and if the temperature of the preform 1 is more than 70° C., inconveniences such as deformation of the mouth portion 1a of the preform 1 occur, and therefore the temperature of aseptic hot air is preferably not more than 140° C.

As shown in FIG. 10(J), aseptic air is blown out from a slit-shaped blow-out opening 85a formed in a box-shaped manifold 85b that is the main body of the air blasting nozzle 85. Further, the air blasting nozzle 85 may be made to follow the preform 1 to blast aseptic air onto the preform 1. Further, the air blasting nozzle 85 may be formed into a rod shape and inserted into the preform 1 so that aseptic air is blasted to the interior of the preform 1 to remove foreign matters in the preform 1 at the same time.

Sterilizer gas blasting to the preform 1 as shown in FIG. 10(I) is performed with the preform sterilizer gas blasting nozzle 83 provided in the wheel 7 as shown in FIG. 9, and the blasting of aseptic air to the preform 1 as shown in FIG. 10(J) is performed with the air blasting nozzle 85 provided in the wheel 8 as shown in FIG. 9. However, both processes may be performed with the wheel 7 or the wheel 8.

The preform 1 supplied to the heating portion 6 reaches a heating portion conveying wheel 9 shown in FIG. 9. Thereafter, the heating step of the preform 1 is the same as that in Embodiment 1. The heated preform 1 is conveyed to the molding portion 16 via the wheel 15 as shown in FIG. 9. A preform tunnel 86 surrounding the conveying path of the preform 1 is provided in the conveying path of the wheel 15 as shown in FIG. 9. The preform tunnel 86 covers the mouth portion 1a of the preform 1 from above, and its ceiling portion is formed into a roof shape having an inclined surface. Further, in the ceiling portion, nozzles that blow out aseptic air toward the mouth portion 1a of the preform 1 are provided in a row of pipes, or a slit shape. As a result, aseptic air is efficiently supplied to the preform 1, and the preform 1 is passed to the molding wheel 18 of the molding portion 16 while maintaining the aseptic condition.

The molding step of the preform 1 passed to the molding wheel 18 is the same as that in Embodiment 1.

While the molded container 2 is conveyed to an inspecting portion 78 via a wheel 23, a container tunnel 87 surrounding the conveying path of the container 2 is provided in the conveying path in the wheel 23 as shown in FIG. 9. The container tunnel 87 covers the mouth portion 1a of the container 2 from its above, and the ceiling portion is formed into a roof shape having an inclined surface. Further, in the ceiling portion, nozzles that blow out aseptic air toward the mouth portion 1a of the container 2 are provided in a row of pipes, or a slit shape. As a result, aseptic air is efficiently supplied to the container 2, and the container 2 can travel while maintaining its aseptic condition being in the molding portion chamber 17.

The container 2 is passed to the inspection wheel 88 of the inspecting portion 78 via the wheel 23. Only the container 2 which has been confirmed not to have any defect is further conveyed to the filling portion 39. It is preferable that the container 2 is inspected by the inspecting portion 78 such that an improper product is not produced by using an abnormal container 2 attributable to molding defects or the like. When an abnormality is found by the inspection, the container is discharged to the outside of the aseptic filler by the discharge apparatus 89 for defective containers shown in FIG. 9. Inspection equipment 24 for inspecting the container 2 is provided along the inspection wheels 88 and 90 of the inspecting portion.

The inside of the inspecting portion chamber 80 is sterilized before operation, and aseptic air is supplied during operation to maintain an aseptic atmosphere. In sterilization before the operation of the aseptic filler, the inspection equipment 24 is housed in a closed container so that the inspection equipment 24 for inspecting the container 2 does not come into contact with the sterilizer. This is to prevent the inspection equipment 24 from coming into contact with the sterilizer and causing corrosion or the like. That is, the inspecting portion 78 includes the inspection equipment 24 housed in a closed container. While inspection items and inspection process are the same as those in Embodiment 1, since the container 2 has already been sterilized, temperature measurement may not be performed.

While the container 2 which has been determined to be abnormal by the inspection is discharged to the outside of the aseptic filler by the discharge apparatus 89 provided on the discharge wheel 91, the container 2 which has been determined to be normal is conveyed to the filling portion 39 via the wheel 92. The process steps in the filling portion 39, the sealing portion 44, and the discharging portion 47 are the same as those in Embodiment 1.

Before the operation of the aseptic filler, the interiors of the heating portion chamber 12 and the molding portion chamber 17 are sterilized. For example, as one of sterilization methods, the interiors of the heating portion chamber 12 and the molding portion chamber 17 are gas sterilized with air containing hydrogen peroxide at a concentration of 20 mg/L or less. In this case, the heating portion chamber 12 and the molding portion chamber 17 are provided with the sterilizer spraying nozzle 58 as shown in FIG. 5 as in Embodiment 1. Further, the area with which the preform 1 or the container 2 comes in contact may be irradiated with a UV lamp (ultraviolet sterilization). Further, the interior of the molding portion chamber 17 may be sterilized by introducing a liquid sterilizer into the preform 1 by a method such as dropping, blowing air or the like into the preform 1 from the blow nozzle 21 while the sterilizer remains inside the preform 1, and thereby causing the sterilizer to be diffused into the molding portion chamber 17. In the sterilization of the heating portion chamber 12 and the molding portion chamber 17 with hydrogen peroxide, rinsing of the interiors of the chambers with aseptic water may not be performed because the sterilizer is unlikely to remain therein.

Aseptic air is supplied to the interiors of the heating portion chamber 12 and the molding portion chamber 17 in order to maintain the aseptic condition in the heating portion chamber 12 and the molding portion chamber 17 while the aseptic filler is operated. As in Embodiment 1, the heating portion chamber 12 and the molding portion chamber 17 each include an aseptic air supply apparatus 60.

The inspecting portion chamber 80 includes a sterilizer spraying nozzle 58, a liquid spraying nozzle 59, and an aseptic air supply apparatus 60, as in Embodiment 1 shown in FIG. 5. Sterilization of the interior of the inspecting portion chamber 80 before operation of the aseptic filler is performed in the same manner as in each chamber in Embodiment 1.

Cleaning and sterilization of the interiors of the filling portion chamber 41, the sealing portion chamber 46, the discharging portion chamber 49, and the outlet portion chamber 53 are the same as those in Embodiment 1. Since the content of the filling portion chamber 41 is scattered in the chamber and are heavily contaminated, an SOP treatment using peracetic acid or an alkaline solution as a sterilizer is performed so that cleaning with aseptic water is required. However, since the contamination of the inspecting portion chamber 80, the discharging portion chamber 49, and the outlet portion chamber 53 is limited, an SOP treatment using only hydrogen peroxide may be sometimes performed. In this case, cleaning with aseptic water may not be performed. Therefore, the aseptic water produced by the content sterilization apparatus 66 is supplied to at least the filling portion chamber 41. Further, at least the filling portion chamber 41 is provided with an aseptic water supply apparatus 70 for supplying aseptic water produced by the content sterilization apparatus 66.

Further, if the interior of the sealing portion chamber 46 is also contaminated with the content, an SOP treatment using a sterilizer such as peracetic acid or an alkaline solution mainly composed of caustic soda is performed. Therefore, aseptic water produced by the content sterilization apparatus 66 is also supplied to the interior of the sealing portion chamber 46.

At least in the filling portion chamber 41, when an SOP treatment is performed before operation of the aseptic filler, the aseptic water supply apparatus 70 supplies aseptic water to each chamber after the sterilizer is sprayed in each chamber, and the sterilizer is washed away.

Embodiments according to the present application have been described with reference to an aseptic filler that molds the preform 1 into the container 2, but it can be applied to the aseptic filler for cups, liquid paper containers, and film packaging in addition to the container to be preform molded.

REFERENCE SIGNS LIST

66 Content sterilization apparatus
67 Surge tank
68 Head tank
70 Aseptic water supply apparatus
71 Aseptic water reservoir tank

The invention claimed is:

1. An aseptic filler, sequentially comprising:
   a container sterilizing portion that sterilizes a molded container;
   an air rinsing portion that air rinses the sterilized container;
   a filling portion that fills the container sterilized with an aseptic atmosphere, with a content sterilized by a content sterilization apparatus;
   a sealing portion that seals the container filled with the content, with a sterilized lid material in an aseptic atmosphere;
   a discharging portion that places the sealed container on a discharging conveyor; and
   further comprises chambers that shield the container sterilizing portion, the air rinsing portion, the filling portion chamber and the discharging portion,
   wherein the aseptic filler comprises an aseptic water supply apparatus that supplies aseptic water which is sterilized by the content sterilization apparatus and sprays to a container sterilizing portion chamber, an air rinsing portion chamber, a filling portion chamber and the discharging portion chamber of the aseptic filler.

2. The aseptic filler according to claim 1, wherein the aseptic water supply apparatus includes a heating apparatus that heats the aseptic water.

3. The aseptic filler according to claim 2,
   wherein the aseptic water supply apparatus includes a sterilization apparatus that sterilizes an interior of aseptic water supply piping for supplying the aseptic water from the content sterilization apparatus to at least the filling portion chamber.

4. The aseptic filler according to claim 2,
   wherein two or more of the content sterilization apparatuses are provided.

5. The aseptic filler according to claim 2,
   wherein the aseptic water supply apparatus is provided with an aseptic water reservoir tank that stores the aseptic water.

6. The aseptic filler according to claim 1, wherein
   the aseptic water supply apparatus includes a sterilization apparatus that sterilizes an interior of aseptic water supply piping for supplying the aseptic water from the content sterilization apparatus to at least the filling portion chamber.

7. The aseptic filler according to claim 6,
   wherein two or more of the content sterilization apparatuses are provided.

8. The aseptic filler according to claim 6,
   wherein the aseptic water supply apparatus is provided with an aseptic water reservoir tank that stores the aseptic water.

9. The aseptic filler according to claim 1, wherein two or more of the content sterilization apparatuses are provided.

10. The aseptic filler according to claim 9,
    wherein the aseptic water supply apparatus is provided with an aseptic water reservoir tank that stores the aseptic water.

11. The aseptic filler according to claim 1, wherein the aseptic water supply apparatus is provided with an aseptic water reservoir tank that stores the aseptic water.

12. A method for cleaning an aseptic filler,
    the aseptic filler sequentially including: a container sterilizing portion that sterilizes a molded container; an air rinsing portion that air rinses the sterilized container; a filling portion that fills the container sterilized with an aseptic atmosphere, with a content sterilized by a content sterilization apparatus; and a sealing portion that seals the container filled with the content, with a sterilized lid material in an aseptic atmosphere; a discharging portion that places the sealed container on a discharging conveyor; and further includes chambers that shield the container sterilizing portion, the air rinsing portion, the filling portion and the discharging portion, wherein interiors of a container sterilizing portion chamber, an air rinsing portion chamber, a filling portion chamber and a discharging portion chamber are cleaned by supplying and spraying aseptic water sterilized by the content sterilization apparatus.

13. The method for cleaning an aseptic filler according to claim 12,
wherein the aseptic water supplied from the aseptic water supply apparatus is heated.

14. The method for cleaning an aseptic filler according to claim 13,
wherein the interior of aseptic water supply piping, which supplies the aseptic water from the content sterilization apparatus to at least the filling portion chamber, is sterilized with a sterilizer.

15. The method for cleaning an aseptic filler according to claim 13,
wherein the aseptic water is supplied from at least one of two or more of the content sterilization apparatuses.

16. The method for cleaning an aseptic filler according to claim 13,
wherein the aseptic water is stored and thereafter supplied.

17. The method for cleaning an aseptic filler according to claim 12,
wherein the interior of aseptic water supply piping, which supplies the aseptic water from the content sterilization apparatus to at least the filling portion chamber, is sterilized with a sterilizer.

18. The method for cleaning an aseptic filler according to claim 17,
wherein the aseptic water is supplied from at least one of two or more of the content sterilization apparatuses.

19. The method for cleaning an aseptic filler according to claim 12,
wherein the aseptic water is supplied from at least one of two or more of the content sterilization apparatuses.

20. The method for cleaning an aseptic filler according to claim 12,
wherein the aseptic water is stored and thereafter supplied.

* * * * *